(12) United States Patent
Laaksonen et al.

(10) Patent No.: US 11,429,808 B2
(45) Date of Patent: Aug. 30, 2022

(54) SYSTEMS AND METHODS FOR SCALABLE SEGMENTATION MODEL TRAINING

(71) Applicant: VARIAN MEDICAL SYSTEMS INTERNATIONAL AG, Steinhausen (CH)

(72) Inventors: Hannu Mikael Laaksonen, Espoo (FI); Jan Schreier, Helsinki (FI)

(73) Assignee: VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 214 days.

(21) Appl. No.: 16/721,465

(22) Filed: Dec. 19, 2019

(65) Prior Publication Data

US 2021/0192279 A1   Jun. 24, 2021

(51) Int. Cl.
  *G06F 9/50* (2006.01)
  *G06K 9/62* (2022.01)
  (Continued)

(52) U.S. Cl.
  CPC ......... *G06K 9/6256* (2013.01); *G06F 9/5077* (2013.01); *G06K 9/6218* (2013.01); *G06N 3/04* (2013.01); *G06N 3/08* (2013.01); *G06V 10/421* (2022.01); *G16H 30/20* (2018.01); *G16H 30/40* (2018.01); *G16H 50/20* (2018.01); *G06V 2201/031* (2022.01)

(58) Field of Classification Search
  None
  See application file for complete search history.

(56) References Cited

U.S. PATENT DOCUMENTS

| 8,769,269 B2 | 7/2014 | Anglin et al. |
| 9,165,243 B2 | 10/2015 | Yu et al. |

(Continued)

OTHER PUBLICATIONS

Sun et al., "An Approach to Deep Learning Service Provision with Elastic Remote Interfaces", Jul. 11, 2019, Advances in Databases and Information Systems; Springer International Publishing, Cham, pp. 276-286.

(Continued)

*Primary Examiner* — Soo Shin
(74) *Attorney, Agent, or Firm* — SGPatents PLLC

(57) ABSTRACT

Systems and methods for cloud-based scalable segmentation model training solutions including a computing interface by which a client/user/customer can upload and store training data in a storage device of a cloud-based network, provide access to the training data stored in the storage device, initiate a request for training a segmentation model, monitor the training of the segmentation model, and download the trained segmentation model, and a computing system operatively coupled with a client device through the computing interface and configured to pre-process the training data using a first set of computing resources of the cloud-based network, store the processed training data in a storage device of the cloud-based network, deploy, upon a training request from the client device, a training application on a second set of computing resources of the cloud-based network to train the segmentation model based on the processed training data, provide access to the client device to monitor the training, and provide access to the trained segmentation model.

20 Claims, 16 Drawing Sheets

(51) Int. Cl.
*G06N 3/04* (2006.01)
*G06N 3/08* (2006.01)
*G06V 10/42* (2022.01)
*G16H 30/20* (2018.01)
*G16H 30/40* (2018.01)
*G16H 50/20* (2018.01)

(56) References Cited

U.S. PATENT DOCUMENTS

| | | | |
|---|---|---|---|
| 9,268,550 | B2 | 2/2016 | Stolberg et al. |
| 10,340,046 | B2 | 7/2019 | Baker |
| 10,430,914 | B2 | 10/2019 | Westerhoff et al. |
| 10,445,661 | B2 | 10/2019 | Bendre et al. |
| 10,452,813 | B2 | 10/2019 | Sorenson et al. |
| 10,902,602 | B1* | 1/2021 | Mansi .................. G06T 7/0012 |
| 2013/0212052 | A1 | 8/2013 | Yu et al. |
| 2018/0196654 | A1 | 7/2018 | Bo et al. |
| 2019/0042529 | A1 | 2/2019 | Nurvitadhi et al. |
| 2019/0192880 | A1* | 6/2019 | Hibbard ............... A61N 5/1039 |
| 2019/0205606 | A1* | 7/2019 | Zhou .................... G06N 3/0454 |
| 2020/0293828 | A1* | 9/2020 | Wang .................... G06N 3/063 |
| 2020/0411173 | A1* | 12/2020 | Mansi .................... G16H 50/30 |
| 2021/0081831 | A1* | 3/2021 | Angel .................... G06N 7/005 |
| 2021/0090694 | A1* | 3/2021 | Colley .................. G16H 50/70 |
| 2021/0192279 | A1* | 6/2021 | Laaksonen ........... G06K 9/6256 |
| 2021/0286923 | A1* | 9/2021 | Kristensen ............. G06N 3/088 |

OTHER PUBLICATIONS

International Search Report and Written Opinion dated Mar. 12, 2021, in International Application No. PCT/EP2020/085100.

Jeyavathana et al., "A Survey: Analysis on Pre-processing and Segmentation Techniques for Medical Images," International Journal of Research and Scientific Innovation (IJRSI), vol. 3, Issue 6, Jun. 2016, ISSN 2321-2705.

Li et al., "Privacy-preserving Federated Brain Tumour Segmentation," Nvidia, Biometrical Engineering and Imaging Sciences, King's College London, UK, Oct. 2, 2019.

* cited by examiner

SYSTEMS AND METHODS FOR SCALABLE SEGMENTATION MODEL TRAINING

FIELD

The present disclosure relates generally to medical imaging, and more particularly, to systems and methods for cloud-based scalable segmentation model training.

BACKGROUND

Radiotherapy is an important tool for the treatment of cancerous tumors in patients. Unfortunately, ionizing radiation applied to treat the patient does not inherently discriminate between tumors and proximal healthy structures (e.g., organs-at-risk). Administration of the ionizing radiation thus must be carefully tailored to restrict the applied radiation to the target (i.e., tumor) while avoiding unnecessary irradiation of surrounding anatomy, the goal being to deliver a lethal radiation dose to the tumor while maintaining an acceptable dosage to the proximal structures.

As part of the radiotherapy planning process, medical images of the tumor and surrounding anatomy are obtained. The medical images can serve as a basis for simulations of the radiation treatment and can be used to plan various aspects of the therapy, including but not limited to, beam geometry and location, radiation energy, and dosage. The medical images are typically processed to delineate target regions (e.g., pixels or voxels where a tumor or other regions desired to be irradiated are imaged) and separate surrounding structures (e.g., pixels or voxels where an organ-at-risk (OAR) or other anatomical structure to avoid being irradiated is imaged). This delineation, termed contouring or segmenting, involves defining a respective border defining outlines of the different anatomical structures in the image. However, if anatomical structures are improperly contoured in the images, this could result in insufficient irradiation of the target and/or undesirable irradiation of surrounding structures.

Manual contouring of structures in medical images can be a time-consuming phase in the radiotherapy planning process. To address this issue, automatic segmentation models, such as deep learning segmentation models, have been proposed. Deep learning based segmentation methods are automatic segmentation methods that utilize many layers or stages of nonlinear data processing for feature learning as well as pattern analysis and/or classification.

Generally, deep learning segmentation methods involve a training phase and an inference phase, as shown in FIG. 1. In the training phase, a deep neural network (DNN) model uses training data sets (10) of medical images to generate a particular output (20). For example, the training data set (10) can include 2-D or 3-D images with ground truth contours for the anatomical structures imaged by the different pixels or voxels. During the inference phase, the trained DNN model operates (40) on medical image(s) (30) of a patient to automatically process features of the medical image(s) (50).

Since deep learning based segmentation methods are strongly dependent on the data set they train on, they are not guaranteed to generalize to other datasets. This may lead to suboptimal contouring when a segmentation DNN model is trained on a dataset generated at one clinic, but it is applied on patient data generated at other clinics, or on patient data generated on patients from different geographic regions, for example. Moreover, since different clinics have different contouring practices, a segmentation DNN model which performs well at one clinic might not be accepted at another clinic.

Embodiments of the disclosed subject matter may address one or more of the above-noted problems and disadvantages, among other things.

SUMMARY

Embodiments of the disclosed subject matter provide model training solutions to allow remote clients/users/customers the ability to train segmentation models on their own training datasets.

Embodiments of the disclosed subject matter also provide model training solutions to allow remote clients/users/customers the ability to apply trained segmentation models on their own or on other datasets.

In embodiments, the model training solutions are cloud-based training solutions.

In embodiments, the cloud-based model training solutions are scalable training solutions.

In embodiments, the training can be scaled based on need, and/or number of segmentation requests, and/or size of data, and/or size of the model.

Embodiments of the disclosed subject matter further provide a computing infrastructure for supporting application of cloud-based model training scalable solutions.

In embodiments, the computing infrastructure comprises systems and methods supporting the cloud-based scalable training solutions.

In embodiments, the system may comprise a computing interface by which a client/user/customer can upload and store training data in a storage device of a cloud-based network; provide access to the training data stored in the storage device; initiate a request for training a segmentation model; monitor the training of the segmentation model; and download the trained segmentation model.

In embodiments, the system may also comprise a computing system operatively coupled with a client device through the computing interface and configured to pre-process the training data using a first set of computing resources of the cloud-based network; store the processed training data in a storage device of the cloud-based network; deploy, upon a training request from the client device, a training application on a second set of computing resources of the cloud-based network to train the segmentation model based on the processed training data; provide access to the client device to monitor the training; and provide access to the trained segmentation model.

In embodiments the computer interface is a web-based interface.

In embodiments, the first set of computing resources include a computing device, a computing server, or a virtual machine, and the second set of computing resources include one or more virtual machines.

In embodiments, the second set of computing resources include a scalable cluster of computing engines including a managing computing engine and a plurality of working computing engines, the cluster being configured to be scaled up or down based on the number of segmentation model training requests.

In embodiments, the training application includes machine learning frameworks configured to support deployment of data and computations across different platforms and different tasks.

In embodiments, the segmentation model to be trained is provided by the client/user/customer device.

In embodiments, the segmentation model to be trained is selected by a user via the computer interface from a segmentation model database provided by the computing system.

In embodiments, the segmentation model is an automatic segmentation model.

In embodiments, the automatic segmentation model is a segmentation neural network model.

In embodiments, the training can include training the segmentation neural network model to approximate contours of different anatomical structures in medical images.

In embodiments, the computing system may provide output checkpoints at different intervals during training or at the request of the user, so that the user may monitor the training process.

In embodiments, the computing system can provide access to information regarding training progress, training performance, and training completion.

In embodiments, the system is configured to apply the trained segmentation model on a dataset obtained from the client user; apply another segmentation model on the same dataset; compare the segmentation results to obtain a comparison result; and evaluate the comparison result against a predetermined threshold value.

In embodiments, the system is configured to apply the trained segmentation model on a dataset obtained from the client device; and evaluate the segmentation result against a predetermined threshold value.

In embodiments, the system can provide access to a training log for the monitoring of the training process and a model file for downloading the trained segmentation model.

Embodiments of the disclosed subject matter also provide a system and method for training a segmentation model, the system comprising a web-based computer interface to allow a client user to select training data from a remote database and to initiate a request to train a segmentation model using the selected training data, and a computing infrastructure configured to pre-process the selected training data, deploy a training application to train the segmentation model based on the processed training data, and provide access to the trained segmentation model for further use by the user.

In embodiments, the user may further apply the trained segmentation model to generate contours on medical images of a patient.

Embodiments of the disclosed subject matter also provides a computing platform configured to: access training data stored in a storage device of a cloud-based network; pre-process the training data using a first set of computing resources of the cloud-based network, and store the processed training data in the storage device; deploy a training application on a second set of computing resources of the cloud-based network to train the segmentation model based on the processed training data; provide access to monitor the training of the segmentation model; and provide access to the trained segmentation model.

Embodiments of the disclosed subject matter also provide methods for scalable cloud-based training of segmentation models.

In embodiments, the method can comprise uploading and storing training data in a storage device of a cloud-based network; initiating a request for training a segmentation model, the initiation automatically deploying a training application on computing resources of the cloud-based network by which the segmentation model is trained using the stored training data; monitoring the training; and accessing the trained segmentation model.

Embodiments of the disclosed subject matter also provide a non-transitory computer-readable storage medium upon which is embodied a sequence of programmed instructions, and a computer processing system that executes the sequence of programmed instructions embodied on the computer-readable storage medium to cause the computer processing system to execute the model training methods described herein.

In embodiments, the computer-readable storage medium can cause the computer processing system to prompt a client user to upload training data in a storage device of a cloud-based network, provide access to the training data stored in the storage device, and initiate a request for training a segmentation model. The computer-readable storage medium can further cause the computer processing system to pre-process the training data using a first set of computing resources of the cloud-based network, to store the processed training data in a storage device of the cloud-based network, to deploy a training application on a second set of computing resources of the cloud-based network to train the segmentation model based on the processed training data, and to provide access to monitor the training. The computer-readable storage medium can further cause the computer processing system to allow the user to monitor the training process and to access the trained segmentation model.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

Operation of a deep neural network based segmentation model (DNN model) generally involves a training phase (TP) and an inference phase (IP), as shown in FIGS. 1, 2A-2C, for example. As used herein, the terms "deep learning model" or "deep neural network model" refer to a class of computer-based machine-learning algorithms that utilize many layers or stages (in particular, at least two "hidden" layers between input and output layers) of data processing for feature learning, pattern analysis, and/or classification. In general, these DNN models are formed by a layered network of processing elements (referred to as neurons or nodes) that are interconnected by connections (referred to as synapses or weights). The layers of nodes are trained from end-to-end (i.e., from input layer to output layer) to extract feature(s) from the input and classify the feature(s) to produce an output (e.g., classification label or class).

Figure 1:
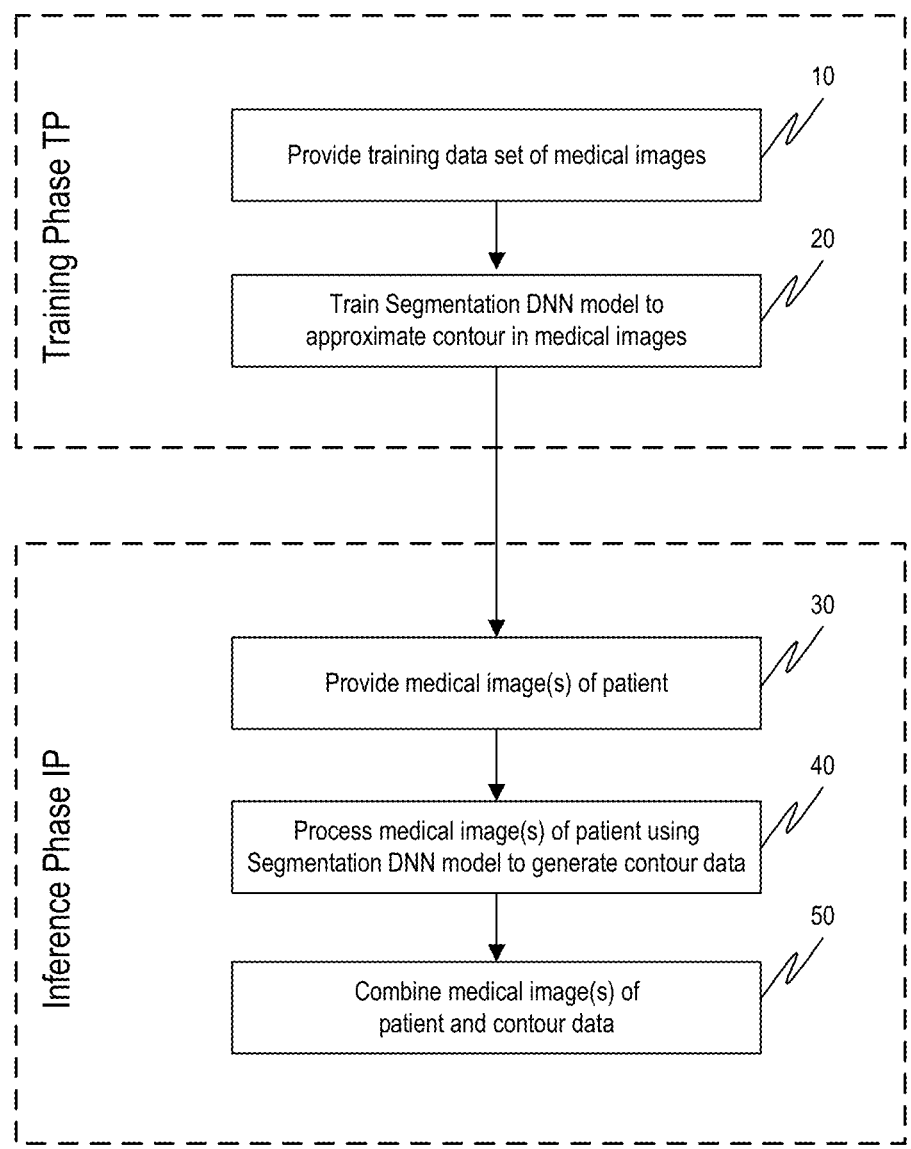
FIGS. 1A, 2A, 2B are simplified schematic diagrams of operation of a neural network model during a training and an inference phase, according to various embodiments of the disclosed subject matter.
Figure 2A:
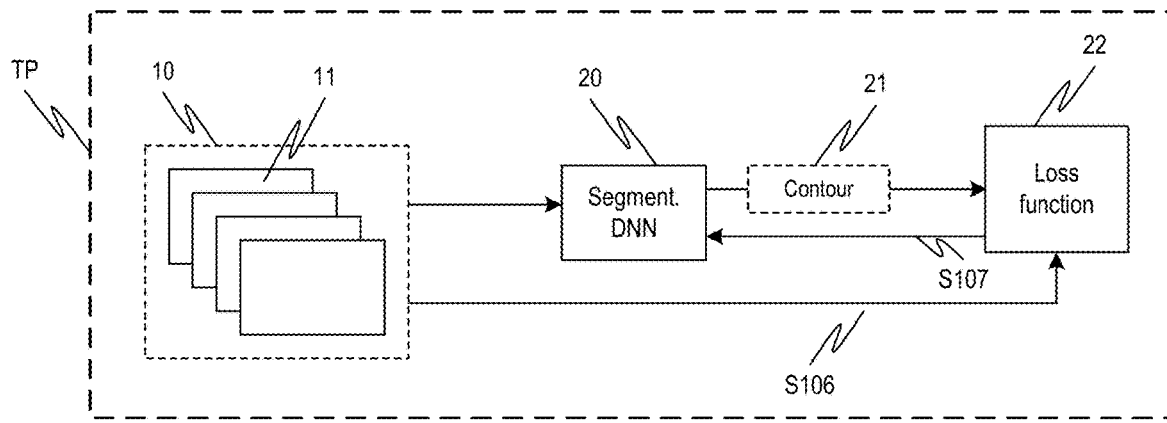
Figure 2B:
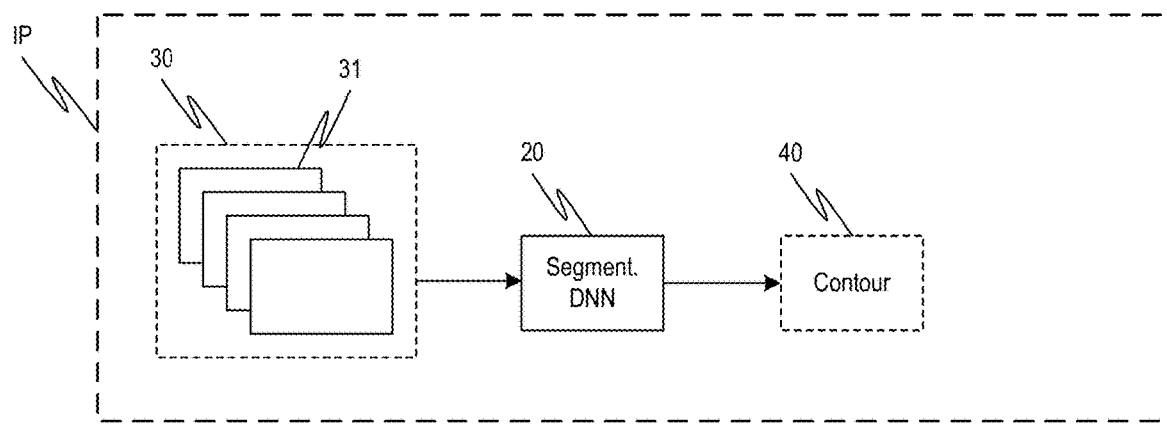
Figure 2C:
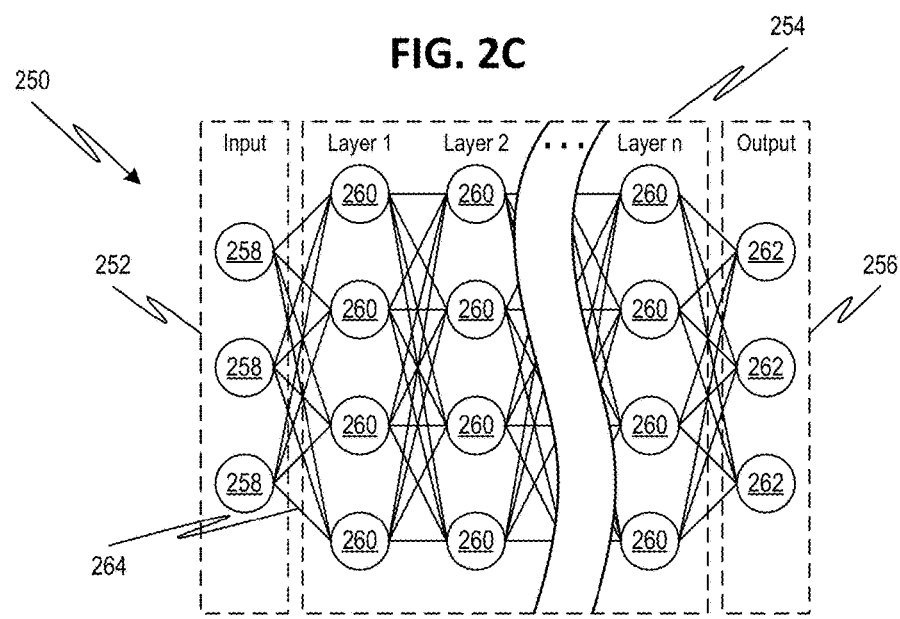
FIG. 2C is a simplified node map of a deep neural network, according to various embodiments of the disclosed subject matter.

FIG. 2C illustrates a simplified node map 250 for an exemplary DNN model. The DNN model includes a stack of distinct layers (vertically oriented in FIG. 2C) that transform an input (provided to the nodes 258 of input layer 252) into an output (at nodes 262 of output layer 256). The intervening layers (Layer 1 through Layer n) between the input layer 252 and output layer 256 are referred to as "hidden" layers 254. At least two hidden layers are provided in order for the neural network to be considered "deep." Each hidden layer has respective nodes 260, which perform a particular computation and are interconnected to nodes in adjacent layers. For example, each node 260 can include a weighting function, which provides weights to respective inputs, and an activation function, which processes the weighted inputs to generate respective outputs. The different hidden layers 254 can include, but are not limited to, final loss layers, non-linear operator layers, pooling layers, subsampling layers, upsampling layers, fully connected layers, and convolutional layers. Although FIG. 2C illustrates the hidden layers 254 as having more nodes 260 per layer than a number of the nodes 258/262 in the input 252 and output 256 layers, other numbers and configurations are also possible. The simplified map illustrated in FIG. 2C is intended to be exemplary only, and other maps based on a selected DNN (e.g., a convolutional neural network) are also possible according to one or more contemplated embodiments.

Generally, in the training phase (TP), the segmentation DNN model 20 uses training data sets 10 of medical images 11 to generate a particular output 21. For example, the training data set 10 can include two-dimensional (2-D) or three-dimensional (3-D) images 11 with ground truth contours for the anatomical structures imaged by the different pixels or voxels. For training of the DNN model 20, the training data set 10 can include additional ground truth information, such as cut-off plane location and/or user-defined ROIs (e.g., bounding boxes), for example. As used herein, "training" refers to determining one or more parameters of nodes in hidden layers of the DNN model 20, for example, by an iterative process S100 illustrated in FIG. 2D, that varies parameters such that the DNN model 20 output 21 more closely matches corresponding ground truth. For example, as shown in FIG. 2C, nodes 260 in the hidden layer 254 can include a filter or kernel, parameters of which (e.g., kernel weight, size, shape, or structure) can be adjusted during the training process.

Figure 2D:
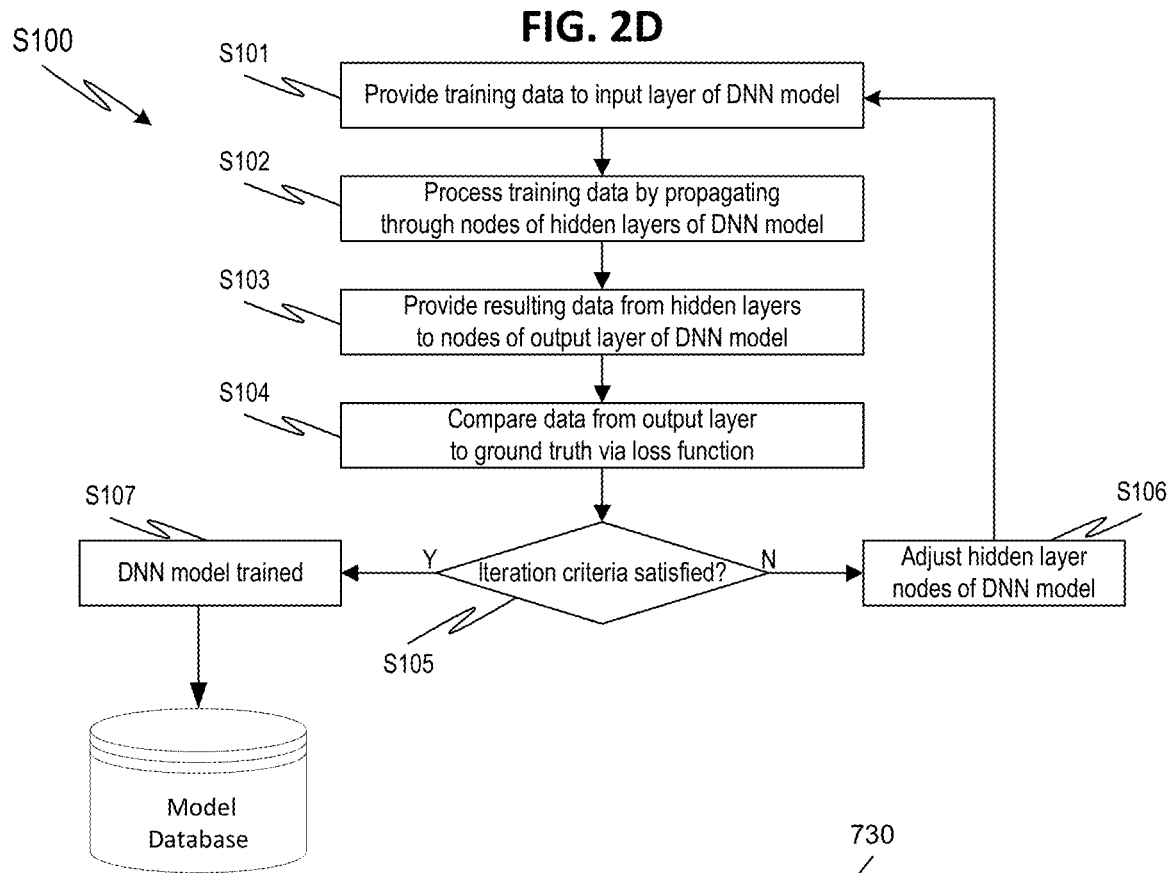
FIG. 2D is a simplified schematic diagram of operation of a neural network model during a training phase, according to various embodiments of the disclosed subject matter.

FIG. 2D illustrates the iterative model training process S100. In step S102, the training data 10 supplied in S101 is propagated through the nodes of hidden layers of an input DNN model. The resulting data from the hidden layer are provided to nodes of the output layer of the DNN mode in S103. In step S104, the data from the output layer is compared with the ground truth via a loss function 22. For example, loss function 22 can be mean-squared error, dice loss, cross entropy-based losses or any other loss function known in the art.

During the training S102, the DNN model is given feedback by loss function 22 on how well its output matches the correct output. Once an iteration criteria is satisfied at S105 (e.g., loss function meets a predetermined threshold, a threshold number of iterations has been reached, or no further improvement is seen between iterations), the DNN model is fixed at S107. Otherwise, the training S100 proceeds to S106, where the DNN model is modified, e.g., by adjusting parameters of the hidden layer nodes, in order to improve the match between output and the desired output. The training process S100 can iterate repeatedly until the desired iteration criteria is met at S105. The DNN model is then considered trained and the trained DNN model of S107 can be stored in an image segmentation model database. A plurality of DNN models can be trained in accordance with this process.

During the inference phase (IP), the trained DNN model 20 can operate on a medical image set 30 containing medical images 31 of a new patient to automatically process features of the medical image(s) 31, such as determining contours 40 of unknown anatomical structures in the image(s). The contoured images may then be used to generate a treatment plan for the patient.

Each respective DNN model may run on a corresponding DNN engine, which refers to any suitable hardware and/or software component(s) of a computer system that is capable of executing algorithms according to any suitable deep learning model. In embodiments, the deep learning model(s) can be based on any existing or later-developed neural network, or combinations thereof. Exemplary neural networks include, but are not limited to, a convolutional neural network (ConvNet or CNN) (e.g., U-Net, deep CNN, LeNet, V-Net, AlexNet, VGGNet, Xception, DenseNet, GoogLeNet/Inception, etc.), residual neural network (ResNet), recurrent neural network (RNN) (e.g., Hopfield, Echo state, independent RNN, etc.), long short-term memory (LSTM) neural network, recursive neural network, generative adversarial neural networks (GANs), normalizing flows and graph networks, and deep belief network (DBN).

To generate the medical images (whether 2-D or 3-D) of the training sets 10 and/or of the patient set 30, any suitable medical imaging modality or modalities can be used, such as, but not limited to, X-ray, computer tomography (CT), cone beam computed tomography (CBCT), spiral CT, positron emission tomography (PET), magnetic resonance imaging (MRI), functional MRI, single photon emission computed tomography (SPECT), optical tomography, ultrasound imaging, fluorescence imaging, radiotherapy portal imaging, or any combinations thereof. For example, image data may include a series of 2-D images or slices, each representing a cross-sectional view of the patient's anatomy. Alternatively, or additionally, image data may include volumetric or 3-D images of the patient, or a time series of 2-D or 3-D images of the patient.

Generally, the image data set 10 which is used to train the segmentation DNN model is generated at a different clinic than the patient data set 30 used for inference. Further, the training data used for training the segmentation model is data of patients that are different from the new patient. Since both the imaging and contouring protocols may be different at different clinics, and since patient anatomies may also differ across different geographic locations, using a segmentation DNN model that was trained at a different location using ground truths that may not be applicable to the current patient, and/or using data of patients that are not compatible with the new patient, and/or using contouring protocols that are not compatible with the contouring protocols of the clinic where the inference process is applied, may generate inaccurate contours for the new patient. Inaccurate contours lead to inaccurate treatment plans for the patient. When executed by a radiotherapy treatment system such as the one shown in FIG. 4, for example, the inaccurate treatment plans lead to inaccurate treatment of the patient.

Figure 3:
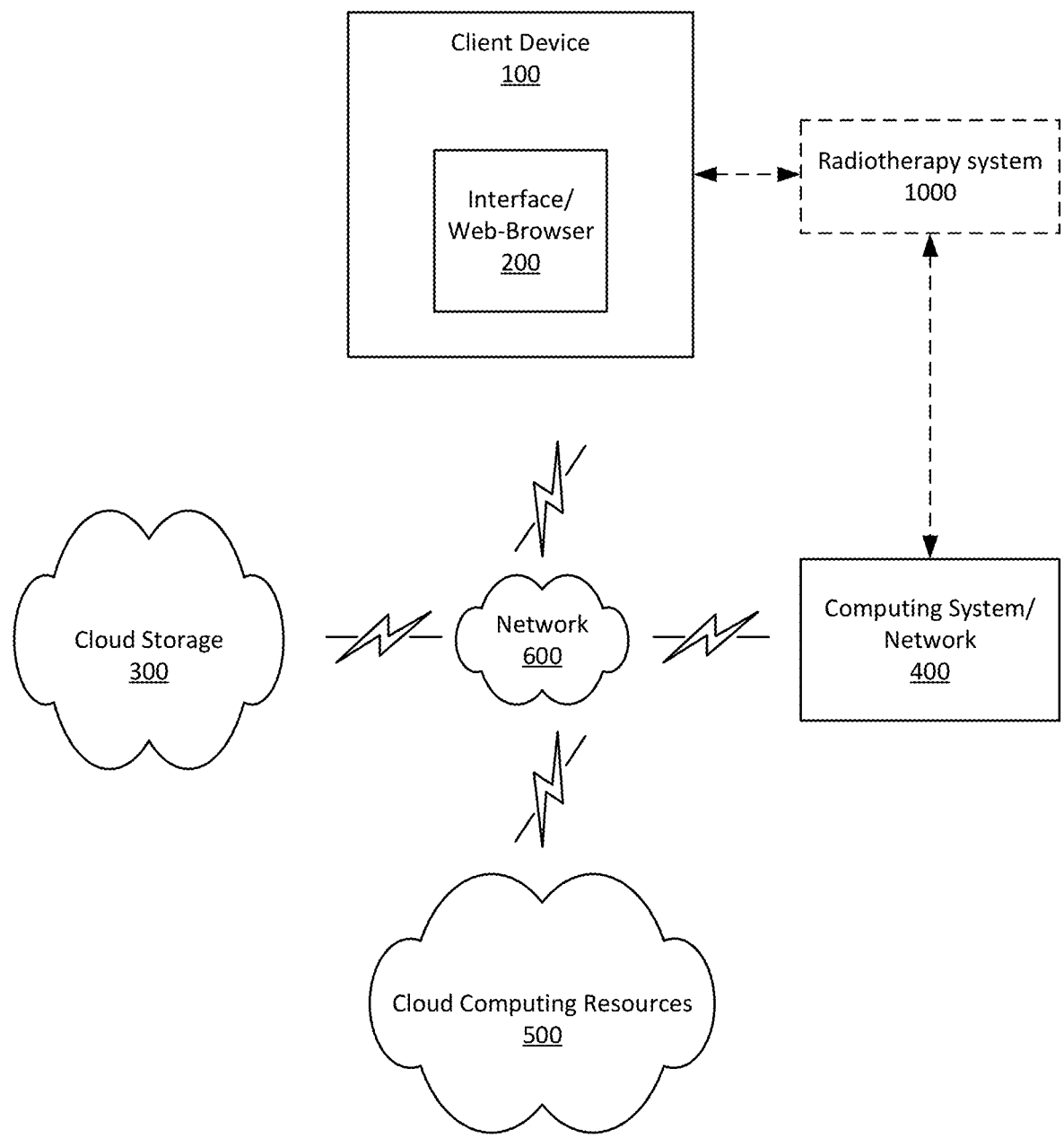
FIG. 3 is a simplified schematic diagram of a cloud-based system for training of a segmentation model, according to various embodiments of the disclosed subject matter.

FIG. 3 illustrates aspects of a computer networking infrastructure that can provide a solution to one or more of these issues. For example, FIG. 3 illustrates a cloud-based training solution whereby a segmentation DNN model can be trained (i.e., training phase) using a training data set generated and/or accepted by the clinic applying the segmentation DNN model (i.e., inference phase).

The computer networking infrastructure of FIG. 3 can also provide a training solution whereby a segmentation DNN model can be trained (i.e., training phase) and applied (i.e., inference phase) using the patient's own data set.

The computer networking infrastructure of FIG. 3 can also provide a training solution whereby a segmentation DNN model can be trained (i.e., training phase) and applied (i.e., inference phase) using a data set generated at the same clinic where the inference data set is generated.

The computer networking infrastructure of FIG. 3 can also provide a training solution whereby a segmentation DNN model can be trained (i.e., training phase) using a segmentation model developed for the patient and/or a previously developed model.

The computer networking infrastructure of FIG. 3 can also provide a training solution whereby a segmentation DNN model can be trained (i.e., training phase) using a previously generated data set.

The computer networking infrastructure of FIG. 3 can also provide a scalable training solution whereby a segmentation DNN model can be trained (i.e., training phase) using computing resources that can be scaled up or down based on need.

The cloud-based training solutions disclosed herein also provide for the application of the trained segmentation DNN models to generate contours of anatomical structures of patients in medical images, and/or to use the contoured images to generate treatment plans for the patients, and/or to use the generated treatment plans on the patients during radiotherapy treatment.

As shown in FIG. 3, the computer networking infrastructure can include a client/user/customer computing device 100, a computing system/network 400, and a cloud networking system including a cloud storage device 300 and cloud computing resources 500, all connected via one or more wired and/or wireless communication links, such as via networks 600. Generally, the client computing device 100 can engage in communication with the cloud storage 300 to securely upload training and/or other patient data into one or more storage devices of the cloud storage 300. The client computing device 100 can also engage in communication with computing system/network 400 to request commencement of a training process to train a segmentation model, such as a segmentation DNN model, for example, based on the training data stored in the cloud storage 300. Upon receipt of the request from the client computing device 100, the computing system/network 400 can engage in secure communication with computing devices of the cloud computing resources 500 to deploy training applications over a range of computing devices to train the segmentation DNN model. The computing system/network 400 is further configured to allow secure downloading of the trained segmentation DNN model by the client computing device 100 for inference, for example.

Figure 5:
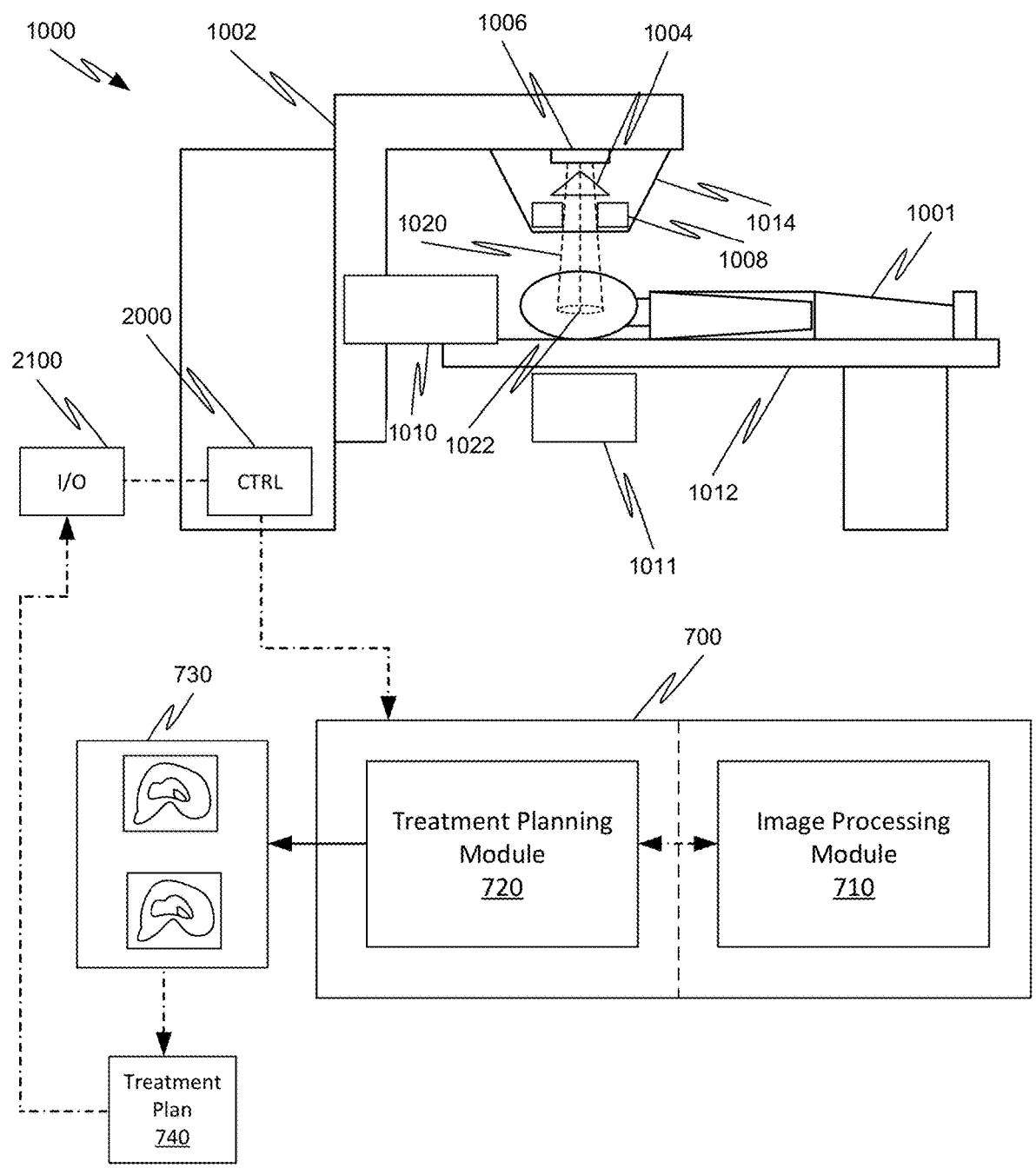
FIG. 5 is a simplified schematic diagram illustrating aspects of a medical image processing and radiotherapy systems, according to various embodiments of the disclosed subject matter.

In an exemplary embodiment, the client computing device 100 is a treatment planning device, such as the treatment planning device 700 shown in FIG. 5, for example, that is configured to perform any suitable number of treatment planning tasks or steps, such as segmentation, dose prediction, projection data prediction, treatment plan generation, etc. When used as such, the client computing device 100 is configured to automatically generate contours using trained segmentation DNN models and to generate a treatment plan 740 for a patient to be executed using a radiotherapy system, such as the radiotherapy system 1000 shown in FIG. 5, for example.

Figure 4:
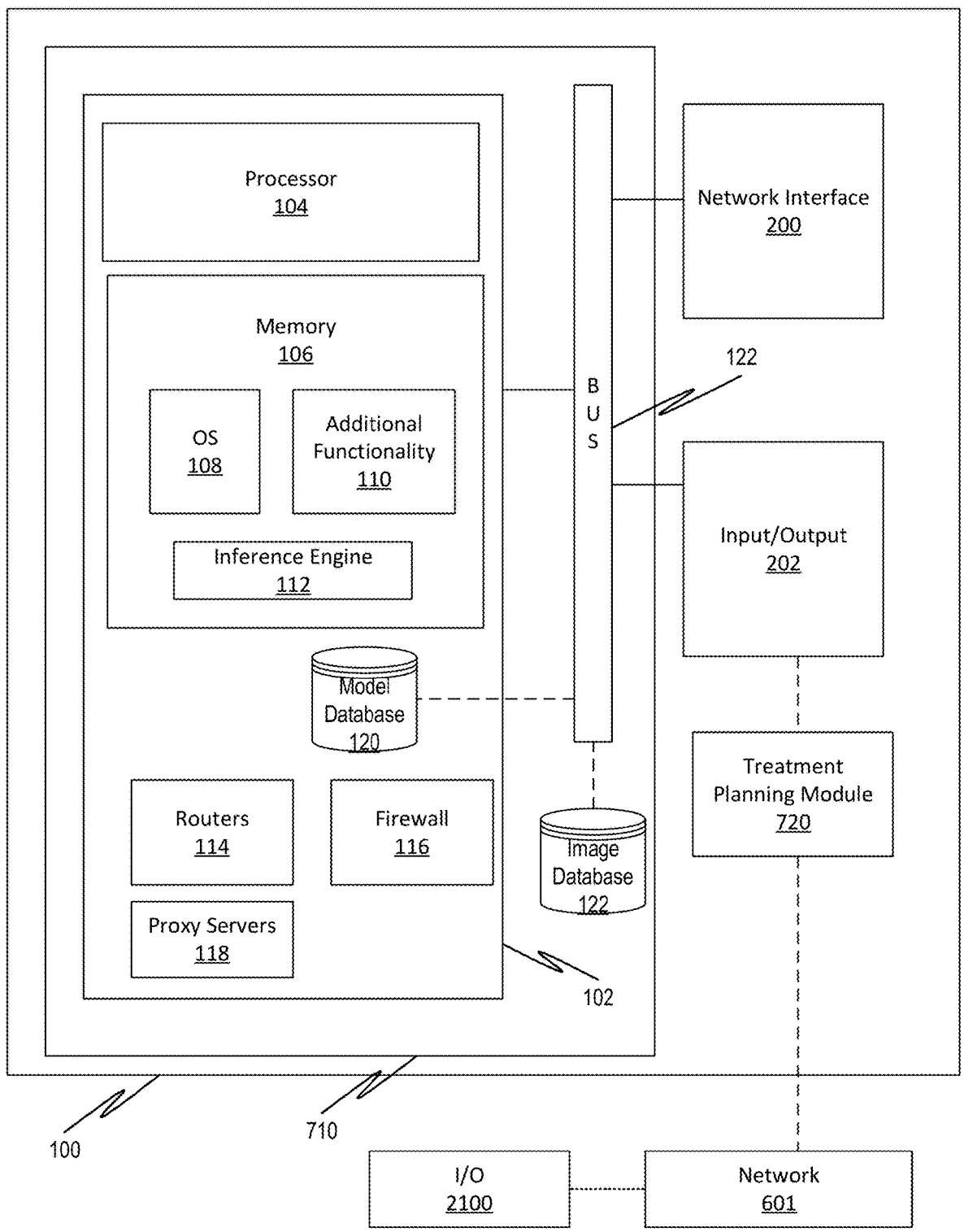
FIG. 4 is a simplified schematic diagram of an image processing system of a client device, according to various embodiments of the disclosed subject matter.

Alternatively, the client computing device 100 can include an image processing module, such as the image processing module 710 shown in FIGS. 4 and 5, for example, to generate contours of anatomical structures of the patient on medical images using trained segmentation DNN models, and a treatment planning module 720 as shown in FIGS. 4 and 5, for example, to generate the treatment plan 740 using the contoured medical images.

Alternatively, the client computing device 100 may provide the image processing functions of the image processing module 710 to generate contours of anatomical structures of a patient, with the treatment planning module 720 being separate from the client computing device 100.

In an exemplary embodiment illustrated in FIG. 4, the client computing device 100 includes an image processing module 710, a treatment planning module 720, a network interface 200, and an input/output device 202 operatively coupled to an input/output interface 2100 of the radiotherapy system 1000 via network 601, for example.

Figure 6:
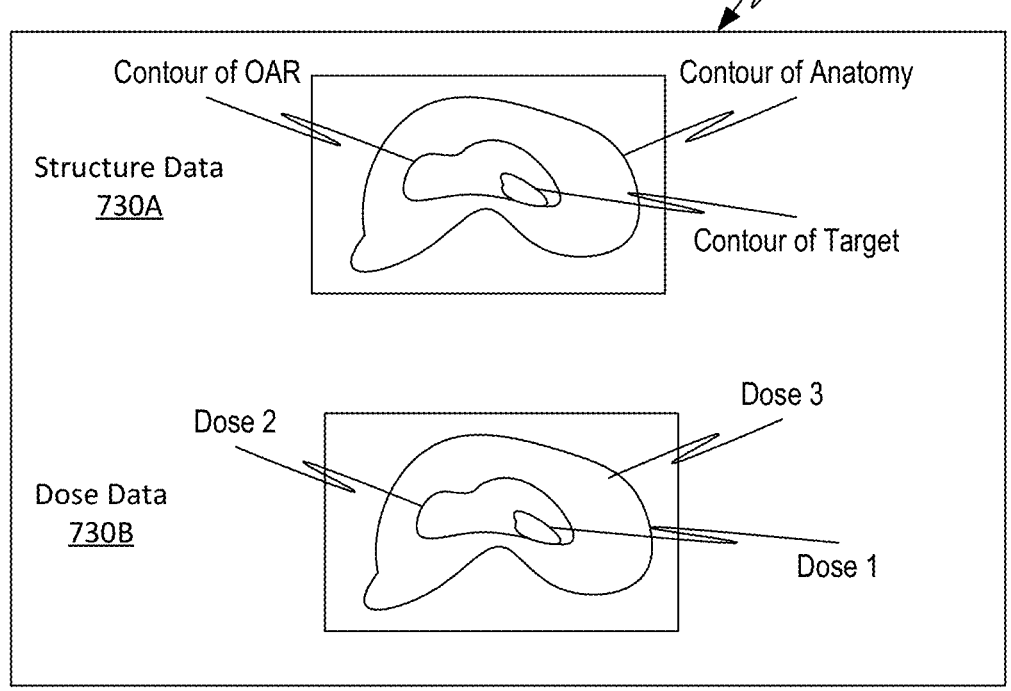
FIG. 6 is a schematic diagram of structure and dose data obtained in a medical image processing, according to various embodiments of the disclosed subject matter.

The image processing module 710 is configured to perform automatic segmentation using trained segmentation DNN models to generate structure data, such as the structure data 730A shown in FIG. 6, for example, identifying various anatomical structures, such as, but not limited to, the malignant tumor (i.e., the target), and any organs-at-risk (OAR), for example, and/or segment/locate anatomical landmarks, and/or segment/locate anatomical or physician intended regions, such as but not limited to, regions that may be used to aid in treatment planning (e.g., nodal regions). The structure data 730A may also identify other anatomical structures, such as other organs, tissues, bones, blood vessels, etc. The structure data 730A may also include any suitable data relating to the contour, shape, size, and location of a patient's anatomy, the malignant tumor (i.e., the target), any organs-at-risk (OAR), and any other anatomical structures.

The image processing module 710 may include a computer system 102 configured to implement the automatic segmentation processes disclosed herein, the computer system 102 including a bus 122 or other mechanism for communicating information between components. The computer system 102 can also include a processor 104, such as but not limited to, a general or specific purpose processor (e.g., graphics processing unit (GPU)), coupled to bus 122. The processor 104 can be a processor of a cloud-based system, and/or a processor of one or more network or Internet host servers. The image processing module 710 can also include an input/output module 202, for example, a communication device such as network interface cards that provide access to network 600 to communicate with the computing system/network 400, or to network 601 to communicate with the radiation therapy system 1000, and/or input/output ports that allow a user to interact with the computer system 102, for example via user input devices including a mouse, keyboard, display, etc., such as an interactive graphical user interface (GUI) for example.

The GUI can include, but is not limited to, user-selectable and/or user-adjustable graphical controls, such as, but not limited to, slider bars, option buttons, text bars, drop-down boxes, windows, animations, and/or any other GUI components for selecting data from an internal and/or external and/or remote dataset, selecting and/or adjusting digital presentations of 3D and/or 2D images and/or image slices, and/or anatomical structures and/or contours of anatomical structures caused to be displayed by the processor 104, selecting to upload and/or download data to and from a cloud-storage device and/or a remote database, display and/or access lists of available segmentation models, and/or lists of supported anatomical structures caused to be displayed by the processor 104 or the computer system 102, or otherwise. The GUI is configured to allow the user to input data, manipulate input and output data, and make any edits to the data, to the generated contours, and to the displayed output. A user can interact with computer system 102 directly or remotely through networks 600, 601 or via any other methods.

The computer system 102 can also include a memory 106 that stores information and instructions to be executed by processor 104. The memory 106 can be comprised of any combination of random access memory (RAM), read only memory (ROM), static storage such as a magnetic or optical disk, or any other type of computer readable media. For example, computer readable media may be any available media that can be accessed by processor 104 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 106 can store software modules that provide functionality when executed by processor 104. The modules can include, for example, an operating system 108 that can provide operating system functionality for the computer system 102, one or more inference engines 112 configured to access and/or link to a plurality of segmentation DNN models, such as those saved in an image segmentation model database 120 of the image processing module 710, or an image segmentation DNN model database 410 of the computing system/network 400, or any other remote segmentation model database made available to the client computing device 100 or the computing system/network 400 or the radiotherapy system 1000. The memory 106 may also include an additional functionality module 110.

The one or more inference engines 112 are modules that include hardware and/or software components that are capable of executing algorithms according to the segmentation models stored in the image segmentation model database 120 or 410 or the remote database, including but not limited to, segmentation DNN models.

One or more of the inference engines 112 can receive medical image data (whether training data or medical image(s) for inference) from an image database 122 of the image computing module 710, or an image database 420 of the computing system/network 400 via network 600, or any other remote image database made available to the client computing device 100 via other networks, or via I/O 202 and network 601 from radiotherapy system 1000, and generate contours for one or more anatomical structures in the received medical images.

The client computing device 100 can further include one or more proxy servers 118, such as but not limited to, servers that facilitate communication and movement of data between the client computing device 100, the remote computing system/network 400, and/or cloud-based networks including the cloud storage 300 and cloud computing resources 500. Proxy servers 118 are also able to establish and maintain secure communication sessions with the computing system/network 400.

The client computing device 100 can further include a firewall 116 configured to deny all communication sessions that are incoming by way of Internet, unless the sessions were initiated from behind the firewall 116 or the firewall 116 has been explicitly configured to support the session. By placing the proxy servers 118 behind the firewall 116, proxy servers 118 may be able to initiate these communication sessions through the firewall 116, and therefore avoid any potential security risks to the client computing device 100.

In embodiments, firewall 116 may include one or more specialized routers 114 or other server devices that protect the client device 100 from unauthorized attempts to access the device, applications, and services therein, while allowing authorized communication that is initiated at the client computing device 100. The firewall 116 may also provide intrusion detection, web filtering, virus scanning, application-layer gateways and any other applications and services.

In one or more embodiments, the client computing device 100 may also include one or more virtual private network (VPN) gateways with which to communicate with the computing system/network 400 and/or the cloud storage 300 and cloud computing 500 services.

The client computing device 100 can also include a network interface 200 configurate to operate a web browser to retrieve, present, and/or navigate through information on the world wide web. The browser may include a web-display tool that provides for or otherwise supports display of information related to segmentation model training including, but not limited to, scalable segmentation model training that can be carried out using the computing system/network 400, and segmentation model inference carried out by the client computing device 100 and/or the computing system/network 400.

The client computing device 100 can also include a treatment planning module 720 to generate dose data 730B, as shown in FIG. 6, specifying the radiation dose to be delivered to the target and any other anatomical structure desired to be irradiated, and specifying the maximum allowable radiation dose that is allowed to be delivered to other anatomical structures, such as the OARs, for example. The treatment plan 740 therefore contains information 730 relating to the structure data 730A and dose data 730B. The treatment plan 740 may also contain any other additional data, such as prescription, disease staging, biologic or radiomic data, genetic data, assay data, past treatment or medical history, or any combination thereof. The treatment plan 740 may also take into consideration constraints imposed on the treatment process by the radiation therapy system 1000 used for delivering the radiation to patient 1001.

An exemplary radiation therapy system 1000 that can be used to deliver radiation in accordance with the treatment plan 740 generated by the client computing device 100 is also shown in FIG. 5. The radiation therapy system 1000 can provide radiation 1022 to the target location 1022 within the patient 1001 positioned on a treatment couch 1012 and can allow for the implementation of various radiation dose verification protocols. The radiation therapy can include photon-based radiation therapy, particle therapy, electron beam therapy, or any other type of treatment therapy.

In an embodiment, the radiation therapy system 1000 can include a radiation treatment device 1010 such as, but not limited to, a LINAC operable to generate one or more beams of megavolt (MV) X-ray radiation 1020 for treatment. The LINAC may also be operable to generate one or more beams of kilovolt (kV) X-ray radiation, for example, for patient imaging. The system 1000 has a gantry 1002 supporting a radiation treatment head 1014 with one or more radiation sources 1006 and various beam modulation elements, such as, but not limited to, flattening filter 1004 and collimating components 1008. The collimating components 1008 can include, for example, a multi-leaf collimator (MLC), upper and lower jaws, and/or other collimating elements. The collimating components 1008 and/or the flattening filter 1004 can be positioned within the radiation beam path by respective actuators (not shown), which can be controlled by controller 2000.

The gantry 1002 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 1014 at various rotational and/or axial positions relative to the patient 1001 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 1008, which can be a computer-controlled mechanical beam shaping device attached to the head 1014 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively, or additionally, the radiation therapy device 1001 can be a tomotherapy device, a helical tomotherapy device, or a simplified intensity modulated arc therapy (SIMAT) device, a volumetric modulated arc therapy (VMAT) device, or a volumetric high-definition (or hyper-arc) therapy (HDRT). In effect, any type of IMRT device can be employed as the radiation therapy device 1010 of system 1000, and can also include an on-board volumetric imaging 1011, which can be used to generate in-treatment image data generated during a treatment session.

Each type of radiation therapy device can be accompanied by a corresponding radiation plan and radiation delivery procedure.

The controller 2000, which can be, but is not limited to, a graphics processing unit (GPU), can include a computer with appropriate hardware such as a processor, and an operating system for running various software programs and/or communication applications. The controller 2000 can include software programs that operate to communicate with the radiation therapy device 1010, which software programs are operable to receive data from external software programs and hardware. The computer can also include any suitable input/output (I/O) devices 2100, which can be adapted to allow communication between controller 2000 and a user of the radiation therapy system 1000, e.g., medical personnel. For example, the controller 2000 can be provided with I/O interfaces, consoles, storage devices, memory, keyboard, mouse, monitor, printers, scanner, as well as a departmental information system (DIS) such as a communication and management interface (DICOM) for storing and transmitting medical imaging information and related data and enabling the integration of medical imaging devices such as scanners, servers, workstations, printers, network hardware, etc.

Alternatively, or additionally, the I/O devices 2100 can provide access to one or more networks, such as network 600 and 601 shown in FIGS. 3 and 4, for example, for transmitting data between controller 2000 and remote systems. For example, the controller 2000 can be networked via I/O 2100 with other computers and radiation therapy systems. The radiation therapy system 1000, the radiation treatment device 1010, and the controller 2000 can communicate with the networks 600 and 601 as well as databases and servers, for example, a dose calculation server (e.g., distributed dose calculation framework) and the client computing device 100. The controller 2000 may also be configured to transfer medical image related data between different pieces of medical equipment.

The system 1000 can also include a plurality of modules containing programmed instructions (e.g., as part of controller 2000, or as separate modules within system 1000, or integrated into other components of system 1000), which instructions cause system 1000 to perform different functions related to adaptive radiation therapy or other radiation treatment. For example, the system 1000 can include a treatment plan module operable to generate a treatment plan for the patient 1001 based on a plurality of data input to the system by the medical personnel, a patient positioning module operable to position and align the patient 1001 with respect to a desired location, such as the isocenter of the gantry, for a particular radiation therapy treatment, an image acquiring module operable to instruct the radiation therapy system and/or the imaging device to acquire images of the patient 1001 prior to the radiation therapy treatment (i.e., pre-treatment/reference images used for treatment planning and patient positioning) and/or during the radiation therapy treatment (i.e., in-treatment session images), and to instruct the radiation therapy system 1000 and/or the imaging device or other imaging devices or systems to acquire images of the patient 1001.

The system 1000 can further include a radiation dose prediction module operable to predict a dose to be delivered to the patient 1001 before commencement of the radiation treatment therapy, a dose calculation module operable to calculate the actual dose delivered to the patient 1001 during radiation therapy treatment, a treatment delivery module operable to instruct the radiation therapy device to deliver the treatment plan to the patient 1001, a correlation module operable to correlate the planning images with the in-treatment images obtained during radiation therapy, a computation module operable to reconstruct three-dimensional target volumes from in-treatment images, an analysis module operable to compute displacement measurements, and a feedback module operable to instruct the controller in real-time to stop radiation therapy based on a comparison of the calculated displacement with a predetermined threshold value (range).

The system 1000 can further include one or more contour generation modules operable to generate contours of target volumes and other structures in pre-treatment (planning, reference) and in-treatment (treatment session) images, an image registration module operable to register pre-treatment images with subsequent in-treatment images, a dose calculation module operable to calculate accumulated dose, a contour propagation module operable to propagate a contour from one image to another, a contour verification module operable to verify a generated contour, a registration deformation vector field generation module operable to determine deformation vector fields (DVFs) as a result of an image deformation process. The system 1000 can further include modules for electron density map generation, isodose distribution generation, does volume histogram (DVH) generation, image synchronization, image display, treatment plan generation, treatment plan optimization, automatic optimization parameter generation, updating and selection, and adaptive directives and treatment information transfer. The modules can be written in the C or C++ programming language, for example. Computer program code for carrying out operations as described herein may be written in any programming language, for example, C or C++ programming language.

Figure 7:
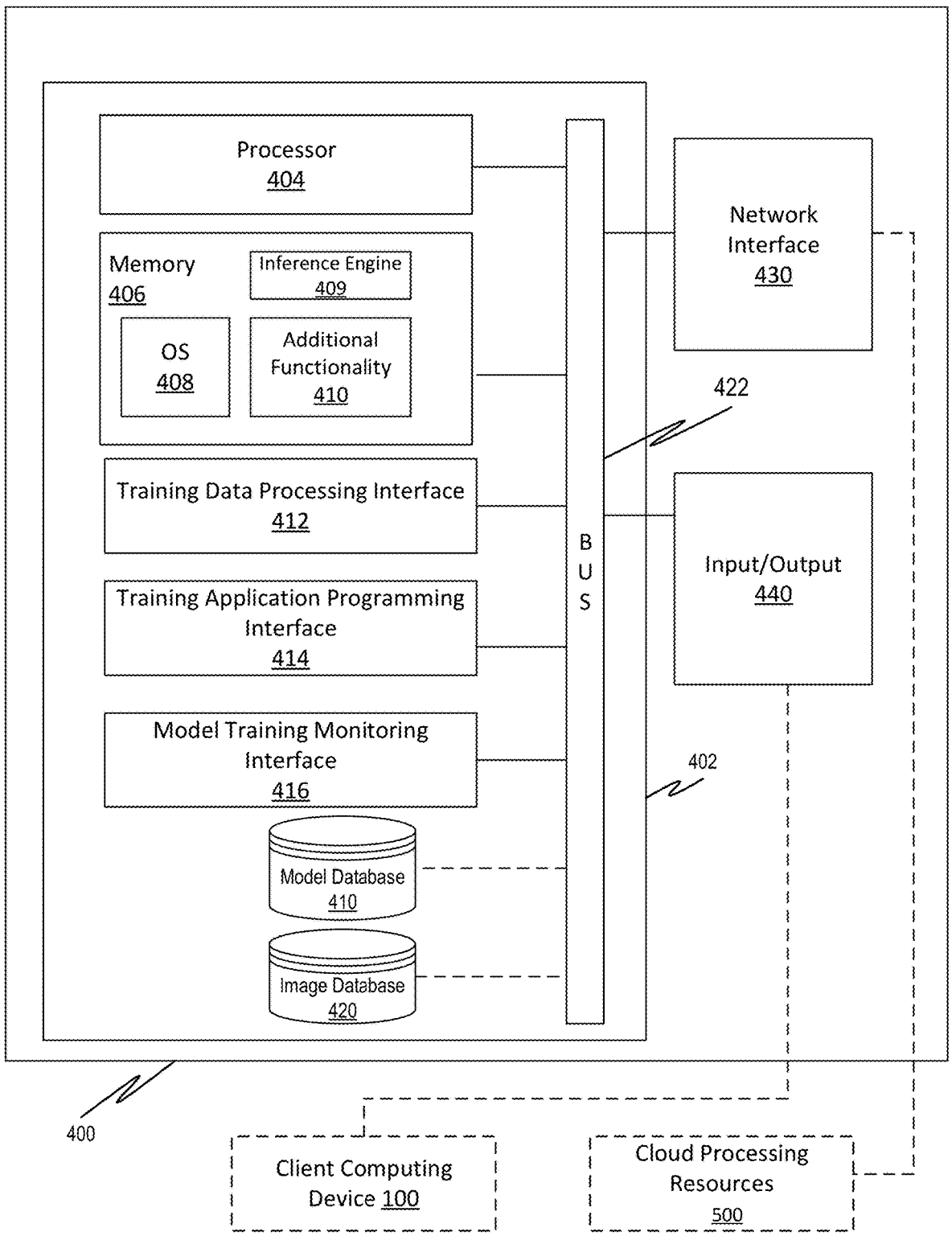
FIG. 7 is a simplified schematic diagram of a computing system/network, according to various embodiments of the disclosed subject matter.

The computing system/network 400 can be a stand-alone computing platform configured to securely communicate with the client device 100, the cloud storage 300, the cloud computing resources 500, and the radiotherapy system 1000 to provide some or all of the web portals, services and/or applications available to the client computing device's network for supporting requests from the client computing device 100, such as but not limited to, cloud-based training and/or inference of segmentation DNN models. The computing system/network 400 can use the cloud storage 300 and the cloud computing resources 500 to deploy applications and services to the client computing device 100. The computing system/network 400 can include a plurality of interfaces and modules, as shown in FIG. 7, for example, that provide a user of the client computing device 100 the ability to request, through the web-browser 200, initialization of a training process to train one or more segmentation DNN models and the deployment of the necessary frameworks, such as but not including CUDA, Tensorflow and Keras, and input data, such as, but not limited to, medical image data and/or processed training data and/or anatomical structure data, on a scalable training infrastructure 520 shown in FIGS. 8A-8C, for example, to execute the training and/or the inference segmentation processes.

Additionally, or alternatively, the computing system/network 400 can provide some or all of the web portals, services and/or applications available to the client device's network for supporting the cloud-based training and the cloud-based application of the trained segmentation DNN models.

Additionally, or alternatively, the computing system/network 400 can be included in the radiotherapy system 1000.

Additionally, or alternatively, the computing system/network 400 can be included in the controller 2000 of the radiotherapy system 1000.

Additionally, or alternatively, the controller 2000 of the radiotherapy system 1000 can fulfill and execute all or a portion of the functions of the computing system/network 400.

An exemplary computing system/network 400 is illustrated in FIG. 7. The computing/network system 400 can include a computer system 402 including a bus 422 or other mechanism for communicating information between components. The computer system 402 can also include a processor 404, such as but not limited to, a general or specific purpose processor (e.g., graphics processing unit (GPU)), coupled to bus 422. The processor 404 can be a processor of a cloud-based system, and/or a processor of one or more network or Internet host servers. The computer system 402 can also include an input/output module 440, for example, a communication device such as network interface cards that provide access to network 600 to communicate with the client computing device 100, or to network 601 to communicate with the radiation therapy system 1000, and/or input/output ports that allow a user to interact with the computer system 402, for example, via user input devices including a mouse, keyboard, display, etc., such as an interactive graphical user interface (GUI) for example.

The computer system 402 can also include a memory 406 that stores information and instructions to be executed by processor 404. The memory 406 can be comprised of any combination of random access memory (RAM), read only memory (ROM), static storage such as a magnetic or optical disk, or any other type of computer readable media. For example, computer readable media may be any available media that can be accessed by processor 404 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 406 can store software modules that provide functionality when executed by processor 404. The modules can include, for example, an operating system 408 that can provide operating system functionality for the computer system 402, and additional functionality modules 410, such as but not limited to, web-based modules such as the model training monitoring interface 416 configured to provide a user of the client computing device 100 the ability to generate reports, view analytics and perform other tasks. The computer system 402 can also include a training data processing interface 412 configured to provide processing instructions to computing devices, such as, but not limited to, one or more of the preprocessing virtual machines 510 illustrated in FIGS. 8A-8C of the cloud-based computing resources 500 to pre-process training data stored in the cloud storage device 300. The computing system/network 400 can also include a training application programming interface 414 configured to deploy instructions to computing devices, such as but not limited to, the scalable training infrastructure 520 of the cloud-based computing resources 500 shown in FIGS. 8A-8C, for example, to train segmentation models based on the processed training data.

The computer system 402 may also include a model database 410 configured to store a library of segmentation DNN models, including segmentation DNN models trained using the cloud-based training solution described throughout this application, and/or segmentation DNN models received from a remote segmentation model database accessible by the computing system/network 400.

The computer system 402 may also include an image database 420 configured to store a library of image data obtained and/or generated by the computing system/network 400. The computing system/network 400 can also include a network interface 430 configured to securely communicate with the cloud storage 300 and the cloud storage resources 500 via network 600.

The cloud storage 300 can include a plurality of storage devices configured to securely store data received from the client device 100, the computing system/network 400 and/or the radiotherapy system 1000. The cloud storage 300 can be an encrypted cloud storage that provides the client computing device 100 the ability to encrypt any of the files and data it sends to the cloud storage 300 to be stored, and to restrict access to any of the data it stores in the cloud storage 300. The cloud storage 300 can also be a cloud storage that complies with global privacy laws. The cloud storage 300 may also be a cloud storage that provides a two-factor authentication and user permission in order to ensure that access to client data is protected.

The cloud computing resources 500, 500A, 500B (FIGS. 8A-C) can include a plurality of computing devices, including but not limited to a plurality of virtual machines, servers, computing clusters, etc. that allow for secure data retrieval, computing, and transfer between the client device 100, the cloud storage 300, the computing system/network 400 and the radiotherapy system 1000.

In one or more embodiments, the cloud computing resources 500, 500A, 500B can include a first set computing devices 510, 510A, 510B dedicated for the pre-processing of training data received from the client computing device 100, and a second set of computing devices 520, 520A, 520B dedicated for the training of segmentation models.

In an exemplary embodiment, the first set of computing devices 510, 510A, 510B may include one or more virtual machines, and the second set of computing devices 520, 520A, 520B may include one or more or a cluster of virtual machines that emulate computing systems and mimic the functionality of physical computers.

Figure 8A:
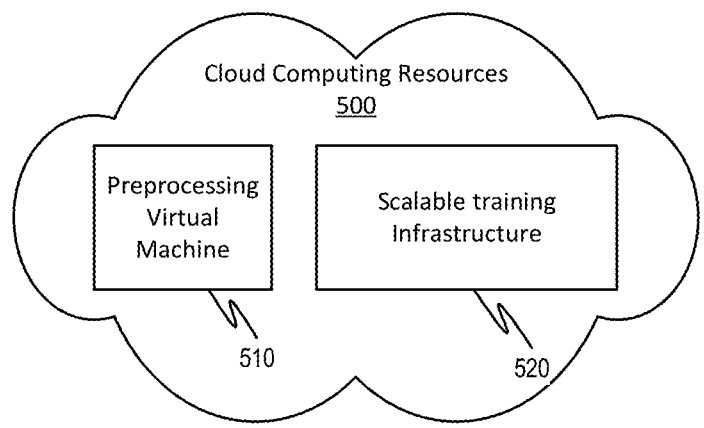
FIGS. 8A-8C are simplified schematic diagrams of cloud-computing resources, according to various embodiments of the disclosed subject matter.
Figure 8B:
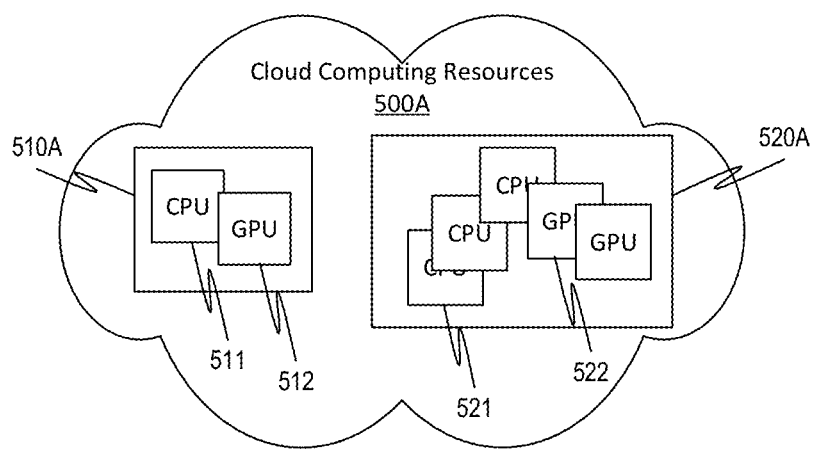

Alternatively, the first set of computing devices 510A may include one or more CPU's 511, and/or one or more GPUs 512, as shown in FIG. 8B, and the second set of computing devices 520A may include a plurality of CPUs 521 and GPUs 522.

Figure 8C:
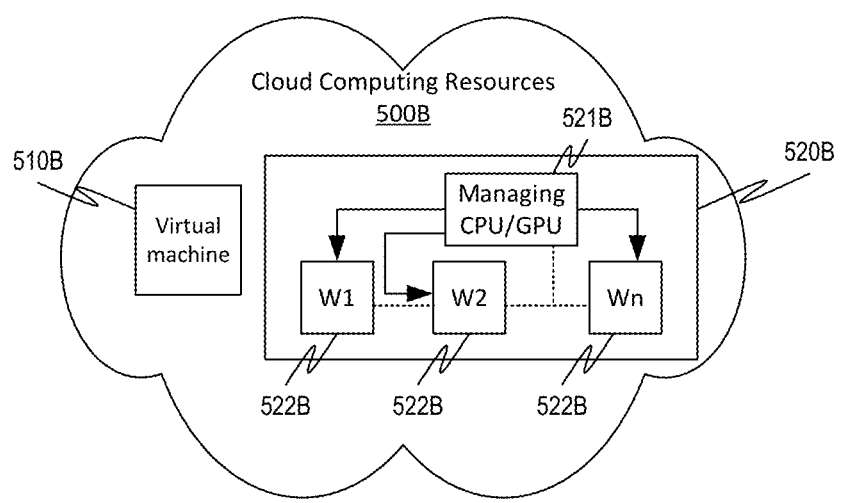

Alternatively, the first set of computing devices 510B may include a virtual machine and the second set of computing devices 520B may include a server cluster 521B supporting a plurality of virtual machines 522B, as shown in FIG. 8C.

In an exemplary embodiment, the second set of computing devices 520B may include a Docker Swarm to establish and manage a cluster of Docker nodes as a single virtual system, and/or Kubernetes so as to be able to deploy the training application in parallel, on Kubernetes, Swarm, and as standalone containers.

In other exemplary embodiments, the second set of computing devices 520B may include a distributed cluster of CPU or GPU enabled virtual machines including a managing CPU/GPU 521B and clusters of virtual working machines 522B which allows for a scalable distribution of the training application(s) across the clusters 522B. Such a distribution is configured to automatically scale with the number of received training requests.

Figure 9:
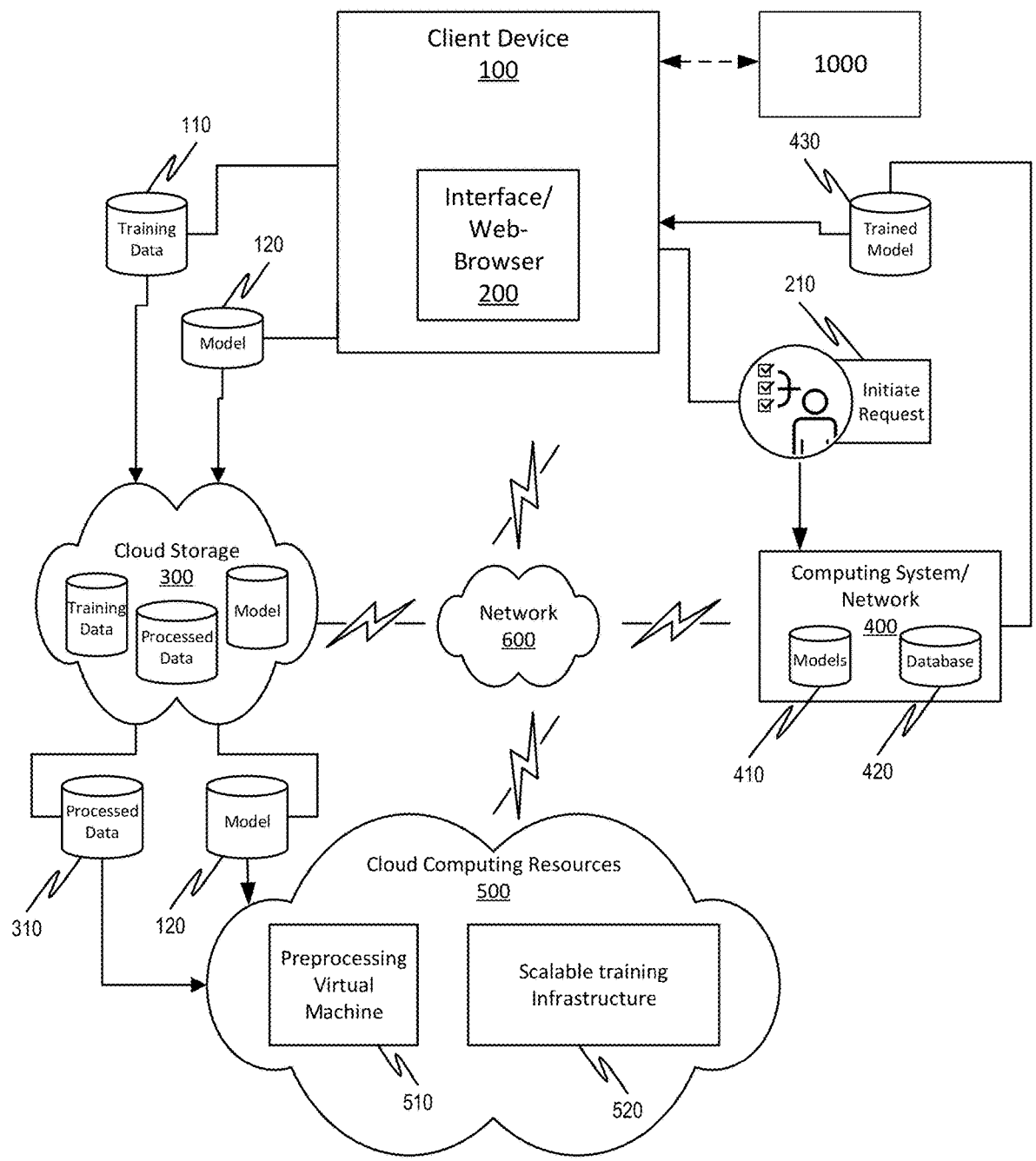
FIGS. 9-11 are simplified schematic diagrams of cloud-based scalable training networks, according to various embodiments of the disclosed subject matter.

FIG. 9 illustrates an exemplary cloud-based training solution whereby a segmentation model 120 is trained using cloud-based resources on a training data set 110 received from the client computing device 100. The segmentation model 120 can be a segmentation DNN model that was stored in the model database 120 of the client computing device 100, or a segmentation DNN model that was stored in the model database 410 of the computing system/network 400 and provided to the client computing device 100, or a segmentation DNN model that was stored in a remote segmentation model database that the client computing device 100 has access to, or a segmentation DNN model that was stored in a remote segmentation model database and the computing system/network 400 has accessed to and provided to the client computing device 100.

The training data set 110 can be a data set that was generated at the client computing device 100 and stored in image database 122, or a data set that was generated at a location different from the client computing device 100 and determined to be acceptable by a user of the client computing device 100 and stored in image database 122 or image database 420 or a remote database, or the patient's own data set configured to be used by the client computing device 100 in the inference phase and stored in image database 122. Alternatively, or additionally, the training data set 110 can be a data set that was generated at a particular clinic/hospital/medical facility, and/or at different clinics/hospitals/medical facilities, and/or different locations within a clinic/hospital/medical facility, and which has been automatically added to a training data base and stored in a central database.

In exemplary embodiments, the training data set 110 can include a set of medical images containing ground truth contours of anatomical structures.

Alternatively, the training data set 110 can include a set of medical images and a set of anatomical structures.

In embodiments, the set of anatomical structures are compiled by a user of the client computing device 100.

In embodiments, the set of anatomical structures are previously compiled anatomical structures that are stored in database 120 or are accessible from a remote database.

The training data set 110 and the segmentation DNN model 120 can be securely uploaded from the client computing device 100 to respective storage devices of the cloud storage 300 via network 600. The user of the client computing device 100 can provide access to the training data 110 and the segmentation DNN model stored in the cloud storage 300 to authorized users.

Through the interface/web-browser 200, and/or a client application, the user of the client computing device 100 may initiate training 210 of the stored segmentation DNN model 120 by selecting a training request option displayed on the display device of the client computing device 100, for example. The client computing device 100 can also provide information to the computing system/network 400 by which the computing system/network can access the stored data in the cloud storage 300.

Upon receipt of the training request 210, the computing system/network 400 is configured to automatically initiate, via the training data processing interface 412, a pre-processing operation on the training data 110 stored in the cloud storage 300 using a first set of computing devices 510. The first set of computing devices 510 can be one or more virtual machines as shown in FIGS. 8A-8C.

Alternatively, the computing system/network 400 does not automatically initiate the pre-processing operation on the training data 110 upon the receipt of the training request 210, but instead waits for a pre-processing request/input/command from the client computing device 100 before it initiates the pre-processing operation.

In exemplary embodiments, the pre-processing operation includes one or more operations to change raw feature vectors of the training data into a representation that is more suitable for the downstream training application. By pre-processing the raw training data 110, the training data 110 can be transformed into a format that can be more easily processed by the computing devices of the scalable training infrastructure 520 to do the training. For example, the pre-processing operation can include one or more of denoising, which removes noise from data, standardization or mean removal and variance scaling, which standardizes the training data by removing outliers, non-linear transformation, which manipulates the raw training data to produce a single input, normalization, which organizes the training data for more efficient access, encoding of categorical features, which codes certain data features as integers, discretization (quantization, binning), which partitions continuous features into discrete values, feature binarization, which can threshold numerical features to get Boolean values, imputation of missing values, which can add values missing from the training data, generating polynomial features, which can generate higher order and interaction items from the training data, and application of custom transformers, which convert an existing function into a transformer to assist in data cleaning or processing. Additionally, or alternatively, the pre-processing operation can include a scaling operation to scale the image resolution to a common image resolution or an image resolution that is more fitting for training.

The computing system/network 400 can determine which pre-processing operation should be applied on the training data 110 based on the data set format beneficial for the training of the segmentation DNN model 120. Upon determination by the computing system/network 400 which pre-processing operations would be beneficial for the stored segmentation DNN model 120, the computing system/network 400 can initiate the appropriate pre-processing operations using one or more virtual machines 510, and/or computer processing units CPUs 511, 512 of the cloud computing resources 500 (500A, 500B).

Alternatively, the system/network 400, may automatically initiate previously determined pre-processing operations.

Alternatively, the system/network 400 may provide an option to the client computing device 100 via the web-browser 200 to select the pre-processing operations to be applied on the training data.

The pre-processing operations can be chosen to apply to one or both medical images and the anatomical structures included in the training data set 110.

Once processed, the processed training data 310 can be stored in the same storage device of the cloud storage 300, so as to be accessible by the computing system/network 400 for the training operation.

The computing system/network 400 can next deploy, via the training application programming interface 414, a training application on the computing resources 520 of the cloud computing resources 500 to execute the training of the segmentation DNN model 120 on the processed training data 310. Deploying of the training application includes deployment of one or more machine learning frameworks, including but not limited to Tensorflow, CUDA, and Keras frameworks, for example, across one or more of the computing resources 520, which then provide the framework necessary to support deployment of the processed training data 310, the segmentation DNN model 120, and training computations across different computing platforms and different tasks. The deploying of the training application further includes providing all or a portion of the processed training data 310 and the segmentation DNN model 120 to the computing resources 520.

Since each segmentation DNN model may generate contours for a plurality of anatomical structures, in order to train the segmentation DNN model 120 to predict contours for desired anatomical structures (i.e., target anatomical structures), which could be anatomical structures that are to be predicted for a patient during inference, instead of providing data relating to the whole set of anatomical structures included in the processed training data set 310 as input to the computing resources 520, the computing system/network 400 is configured to provide a target anatomical structure data set together with the medical images included in the processed training data set 310 as input data to the computing resources 520. Thus, the processed training data set 310 that is provided as input data to the computing resources 520 may include a set of medical images and a set of target anatomical structures.

In embodiments, the user of the client computing device 100 can select one or more anatomical structures from the set of anatomical structures originally compiled/displayed to the user as the target anatomical structures. The selection can be conveyed to the computing system/network 400 via the web-browser 200. Upon receipt of this information, the computing system/network 400 is configured to identify in the processed training data set 310 the data associated with the selected target anatomical structures. This can be automatically done using structure IDs, or manually done by allowing the user to map the anatomical structures. Once the identification is made, the computing system/network 400 is configured to deploy the processed training data set 310 associated with the selected anatomical structures (i.e., target anatomical structures), together with the segmentation DNN model 120 on the computing resources 520.

In embodiments, the selection of the target anatomical structures is initiated by the computing system/network 400 via the web-browser 200.

In embodiments, the selection of the target anatomical structures by the user is automatically sent to the computing system/network 400 as part of the training request 210.

In embodiments, the list of anatomical structures may be provided to the user by displaying on a display screen of the client computing device 100, for example, a list of anatomical structures, and providing the client computing device 100 an option to select the target anatomical structures from the list of anatomical structures. The list of anatomical structures can be automatically provided to the user of the client computing device 100 upon the user initiating a training request 210.

Alternatively, the anatomical structures can be provided to the user by prompting the user to select for display a list of anatomical structures stored in the image database 122, or database 422, or any other remote database available to the client computing device 100, and to manually select the target anatomical structures from the list.

The computing system/network 400 is configured to deploy the training application across as few or as many computing resources 520 of the cloud computing network 500 as is necessary based on the number of training requests received and/or based on the amount of tasks each computing device would need to perform and/or based on the complexity of each request and/or task, for example. The computing system/network 400 is configured to determine the computing resources 520 needed for each request and appropriately scale the computing resources 520. Exemplary deployment and execution of the training processes to obtain trained segmentation DNN models are illustrated in FIGS. 12A-12F.

Once execution of the model training is finished and/or terminated, the trained segmentation DNN model 430 can be provided to the client computing device 100 to be further used for inference to predict contours of anatomical structures for a patient.

In embodiments, the providing of the trained segmentation DNN model 430 includes providing a link to the client computing device 100 so that the trained segmentation DNN model 430 can be downloaded by the client computing device 100 and stored in the database 120.

In embodiments, the providing of the trained segmentation DNN model 430 includes providing a link to the client computing device 100 so that the trained segmentation DNN model 430 can be accessed by the client computing device 100 through the computing system/network 400.

In embodiments, the providing of the trained segmentation DNN model 430 includes providing access to a segmentation service bundle including the trained segmentation DNN model 430 by payment of a service fee.

In embodiments, the providing of the trained segmentation DNN model 430 includes providing access to the trained segmentation DNN model 430 via a software package integrating different segmentation processes.

In embodiments, the trained segmentation DNN model 430 can be stored in database 120 and/or database 420, and/or an accessible remote database, and or the cloud storage 300 to be accessed by the client computing device 100.

The computing system/network 400 is further configured to provide monitoring services to the client computing device 100 via the model training monitoring interface 415. Through this service, a user of the client computing device 100 can monitor via the web-browser 200 the training progress, the training performance and the training completion.

The computing system/network 400 is further configured to deploy an inference process via the inference engine 409 on one or more computing resources 520. For the inference process, the computing system/network 400 may apply the trained segmentation DNN model 320 on the patient data set 30 to generate a first set of contours. Simultaneously or consecutively, the computing system/network 400 may apply another segmentation DNN model, such as a previously trained segmentation model stored in the model database 410, for example, on the patient data set 30 to generate a second set of contours. The computing system/network 400 is further configured to compare the first and second sets of contours and provide the result in the form of a training log, for example, to the client computing device 100, so that the user can compare how well the newly trained segmentation DNN model 430 performs on the patient data as compared to an already available segmentation DNN model performing on the same patient data.

Alternatively, or additionally, the computing system/network 400 may also provide access to live monitoring of the training process as well the option to have the user of the client computing device end the training process when it determines that the segmentation DNN model 310 is satisfactorily trained.

Figure 10:
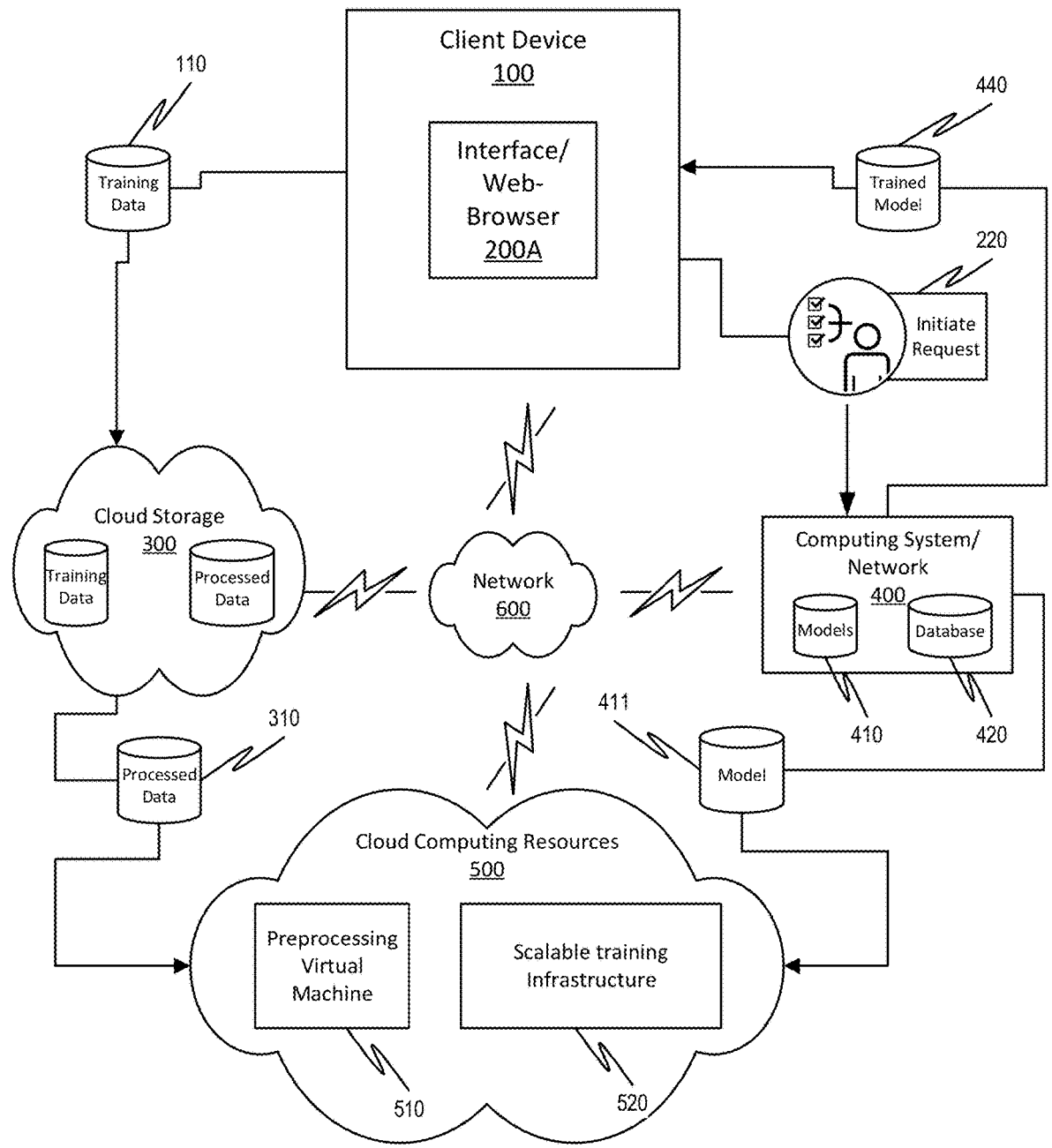

In another exemplary embodiment, as shown in FIG. 10, instead of uploading a segmentation DNN model from the client computing device 100 to the cloud storage 300 to be trained by the computing system/network 400 using the processed training data 310, a list containing a plurality of already trained segmentation models stored in the model database 410 of the computing system/network 400 can be made available via the web-browser 200A to the client for selection. Upon selection of a segmentation DNN model 411 from the list, the user can initiate a pre-processing and a training request 220 as described with reference to the embodiment of FIG. 9, and the pre-processing, training and monitoring steps of FIG. 9 can also be applied.

Additionally, since the trained segmentation DNN model 440 is an already available segmentation model trained on patient data, the user may compare the trained DNN segmentation model 430 with the trained segmentation model 440 and decide which trained segmentation model is better suited for inference.

Optionally, training of the client provided segmentation DNN model 120 and the training of the segmentation DNN model 411 can be simultaneously performed using different computing resources 520, and the training results monitored.

Optionally, the processed training data set 310 can include additional data subsets. For example, data set 310 can include a validation set that is used to track the quality of the segmentation DNN model during training but is not otherwise used as input to the DNN model during training. Alternatively, or additionally, the processed training data set 310 can include a test subset that is only used after training to quantify the quality of the trained model (e.g., accuracy, dice score) and/or to verify that the model has not over-learned or under-learned the data.

Figure 11:
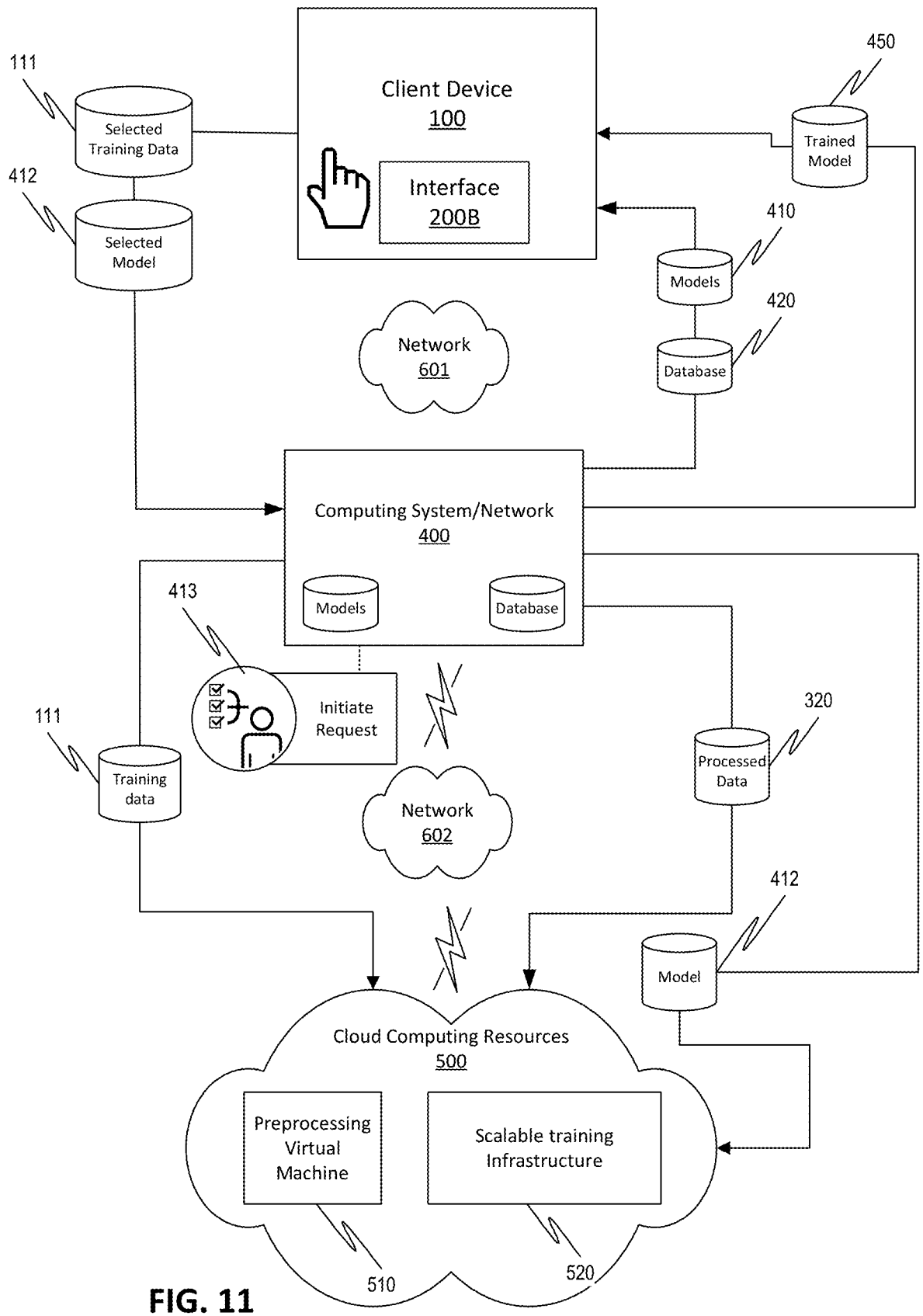

In another exemplary embodiment, as shown in FIG. 11, instead of uploading training data and a segmentation model from the client computing device 100 to cloud storage 300, the user is provided with the option to select, via interface 200B, a training data set 111 from a patient data set stored in database 420, and the segmentation DNN model 412 from the segmentation model database 410 of the computing system/network 400. Once selection is made, the computing system/network 400 can automatically perform the pre-processing of the training data set 111 to obtain the processed training data set 320, and the training of the segmentation DNN model 412 using the processed training data set 320, similar to the pre-processing and training processes described for embodiments of FIGS. 9 and 10.

The trained segmentation DNN model 450 can be provided to the client computing device 100 in similar fashion as previously described.

The computing system/network 400 can also provide information regarding the training progress, training performance, and training completion as previously described.

Figure 12A:
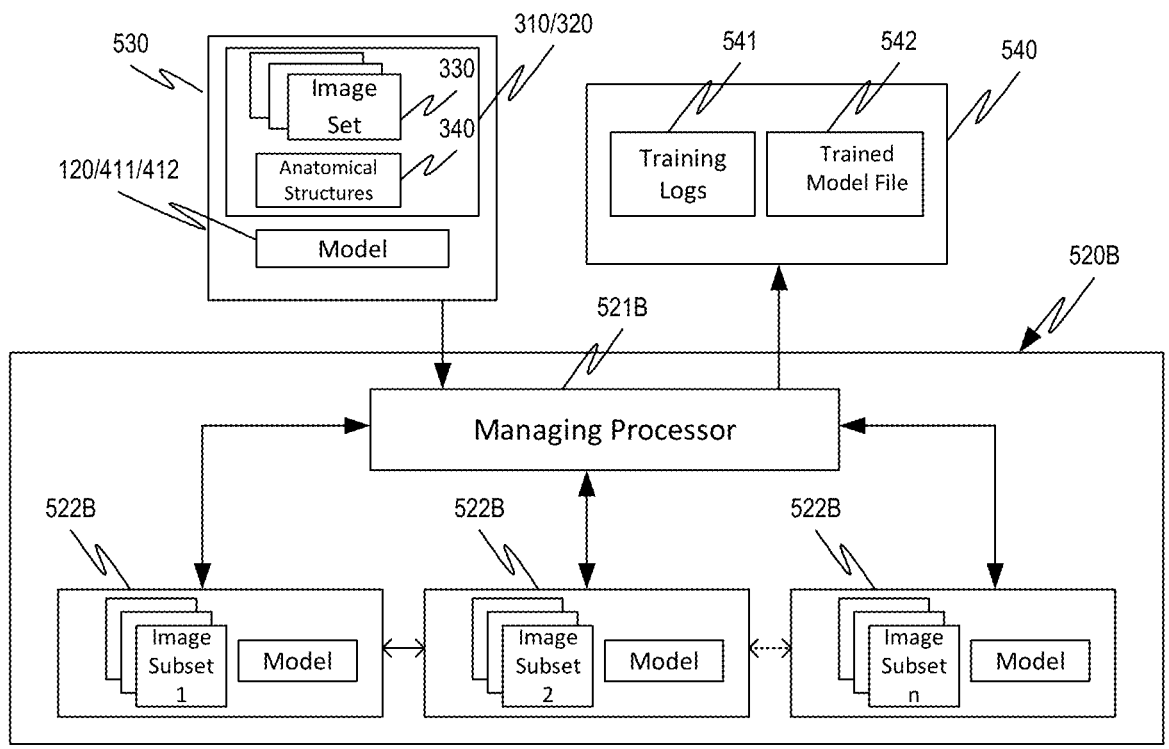
FIGS. 12A-12F are simplified schematic diagrams of distributed segmentation DNN network training using computer clusters, according to various embodiments of the disclosed subject matter.

FIGS. 12A-12F illustrate different deployment configurations of training applications across the scalable training infrastructure 520B. The training infrastructure 520B can be a CPU or GPU managed (521B) cluster (W1-Wn) of working virtual machines 522B. There are several ways to train a segmentation DNN model. FIG. 12A illustrates a data-parallel distributed training process, where the training application 530 containing the processed training data set 310/320, which includes the medical image data set 330 and the target anatomical structure set 340 is deployed across the cluster of virtual machines 522B by the managing processor 521B so that the image data set 330 is divided into n image subsets (Image Subset 1-Image Subset n), each image subset including a portion of the image data set 330, and the segmentation DNN model 120/411/412 is replicated across the n virtual machines 522B. In operation, each of the virtual machines 522B performs forward and backward passes for each image subset. When a virtual machine 522B finishes the process, it shares the updates with the other virtual machines 522B, and the obtained values are used to calculate the updated weights of the entire image data set 330, and the weights are synchronized across the replicated models 120/411/412. The results 540, which can include a training log 541 for the monitoring of the training in progress, and a trained model file 542 for access to the trained segmentation model, can be made accessible to the user of the client computing device 100 via the computing system/network 400. The number n of the virtual machines to be used can be determined based on the size of the image data set 330, for example, and/or other applicable considerations, such as but not limited to, the number of segmentation requests received by the managing processor 521B and/or the number of different segmentation requests received by the managing processor 521B. The number of virtual machines 522B to be used can also be determined based on data size of one or more segmentation requests, and/or size of the segmentation model to be trained, and/or the number of segmentation requests.

Figure 12B:
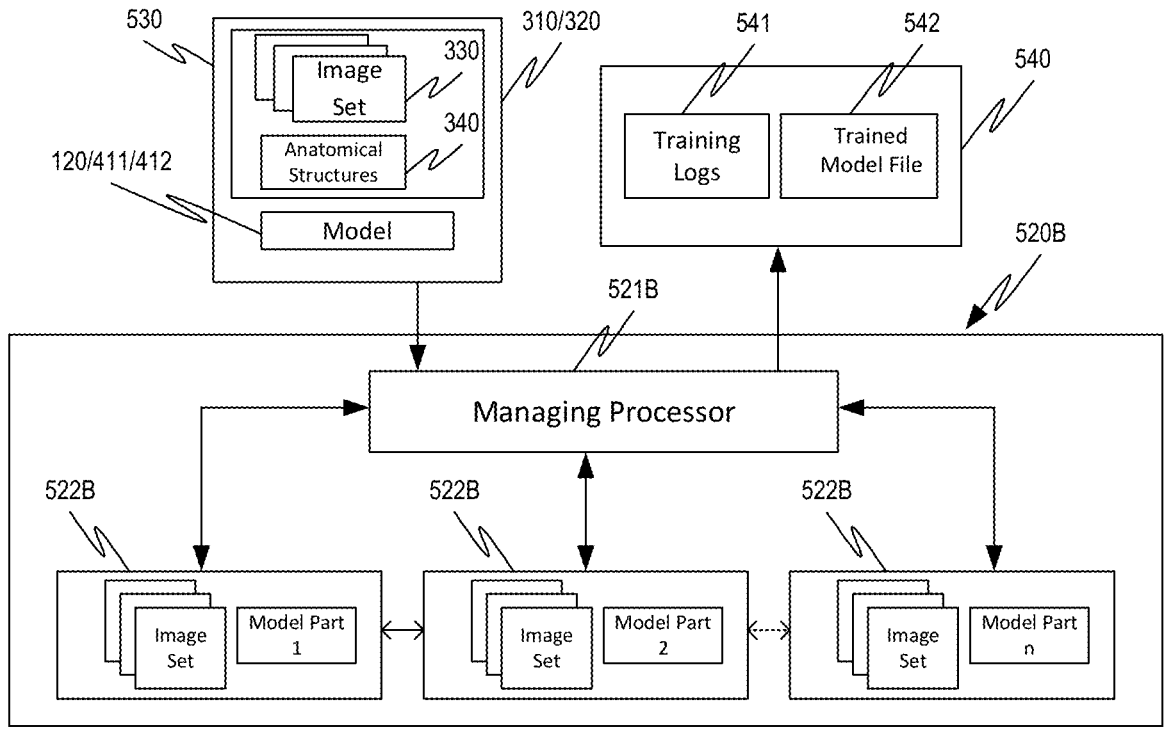

In the model-parallel distributed training process configuration illustrated in FIG. 12B, it is the segmentation DNN model 120/411/412 that is divided across the n virtual machines 522B while the image data set 330 is replicated across the n virtual machines 522B. The segmentation DNN model 120/411/412 can be divided into n model parts (Model Part 1-Model Part n). In an exemplary embodiment, each virtual machine 522B may hold a layer of the DNN network. During the forward and backward pass, the information can be passed between the virtual machines 522B. The results 540 including the training log 541 and the trained model file 542 can be made accessible to the user of the client computing device 100 via the computing system/network 400. The number n of the virtual machines to be used can be determined based on the size of the image data set 330, and/or other applicable considerations, such as but not limited to the number DNN network layers, and/or the number and/or type of segmentation requests received by the managing processor 521B. The number of virtual machines 522B to be used can also be determined based on data size of one or more segmentation requests, and/or size of the segmentation model to be trained, and/or the number of segmentation requests.

Figure 12C:
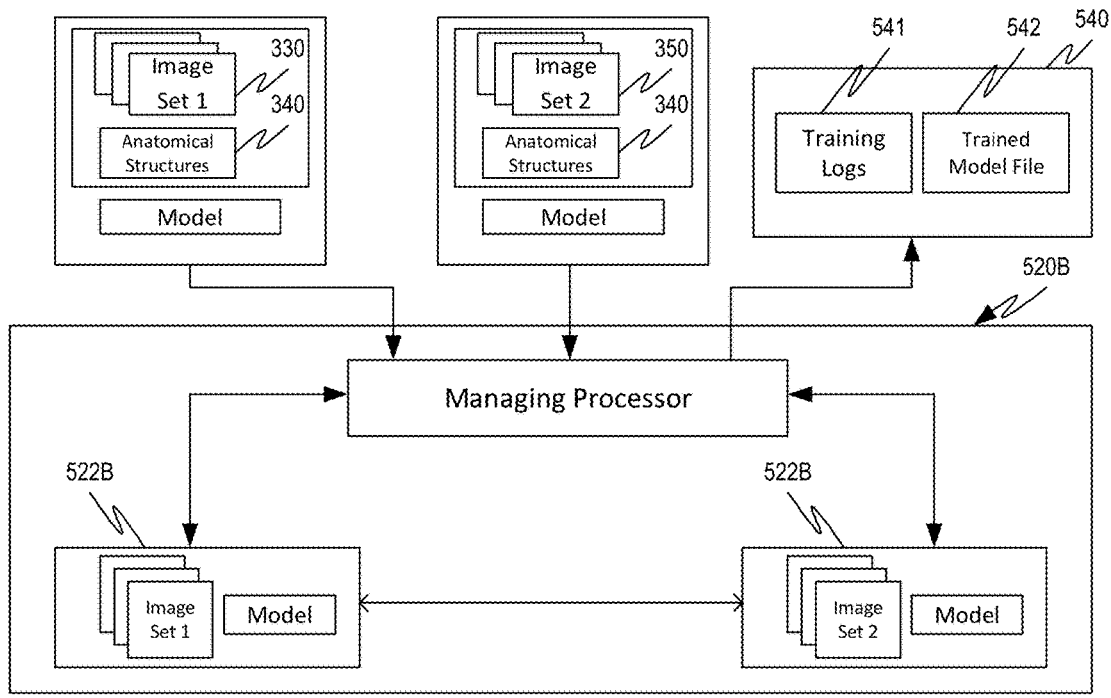

In the configuration illustrated in FIG. 12C, where a first request is made to train a segmentation DNN model using a first image data set 330 and a second request is made to train the same segmentation DNN model using a second data set 350 for the same target anatomical structure set 340, a segmentation application deployment can be made so that the segmentation DNN model is replicated across a first virtual machine 522B and a second virtual machine 522B, with the first virtual machine 522B performing the forward and backward passes for the first image data set 330 and the second virtual machine 522B performing the forward and backward passes for the second data set 350. When the virtual machine 522B finishes the process, it shares the updates with the other virtual machine 522B, and the obtained values are used to calculate the updated weights of both image data sets 330, 350, and the weights are synchronized across the replicated model. The results 540 including a training log 541 and a trained model file 542 can be made accessible to the user of the client computing device 100 via the computing system/network 400. The number of virtual machines 522B to be used can also be determined based on data size of one or more segmentation requests, and/or size of the segmentation model to be trained, and/or the number of segmentation requests.

Figure 12D:
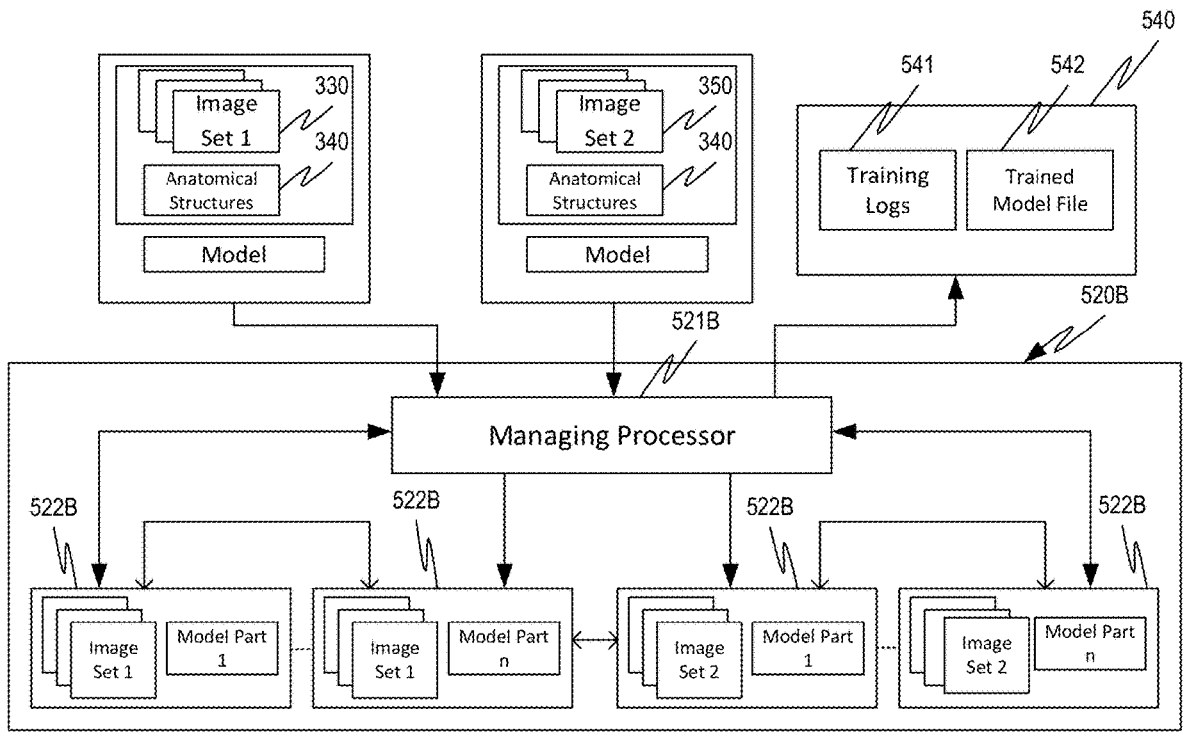

In an alternative configuration, as shown in FIG. 12D, each of the first and second image data sets 330, 350 can be replicated across respective number of virtual machines 522B, and the segmentation DNN model can be divided into respective number of model parts (Model Part 1-Model Part n) for image data set 330, and Model Part 1-Model Part n for image data set 350. Each virtual machine 522B may hold a layer of the DNN network. During the forward and backward pass, the information can be passed between the virtual machines 522B. The results 540 including the training log 541 and a trained model file 542 can be made accessible to the user of the client computing device 100 via the computing system/network 400. The number n of the virtual machines to be used can be determined based on the respective sizes of the image data sets 330, 350 and/or based on other applicable considerations, including but not limited to the number of segmentation requests received by the managing processor 521B, and/or the number of DNN network layers of the model.

Figure 12E:
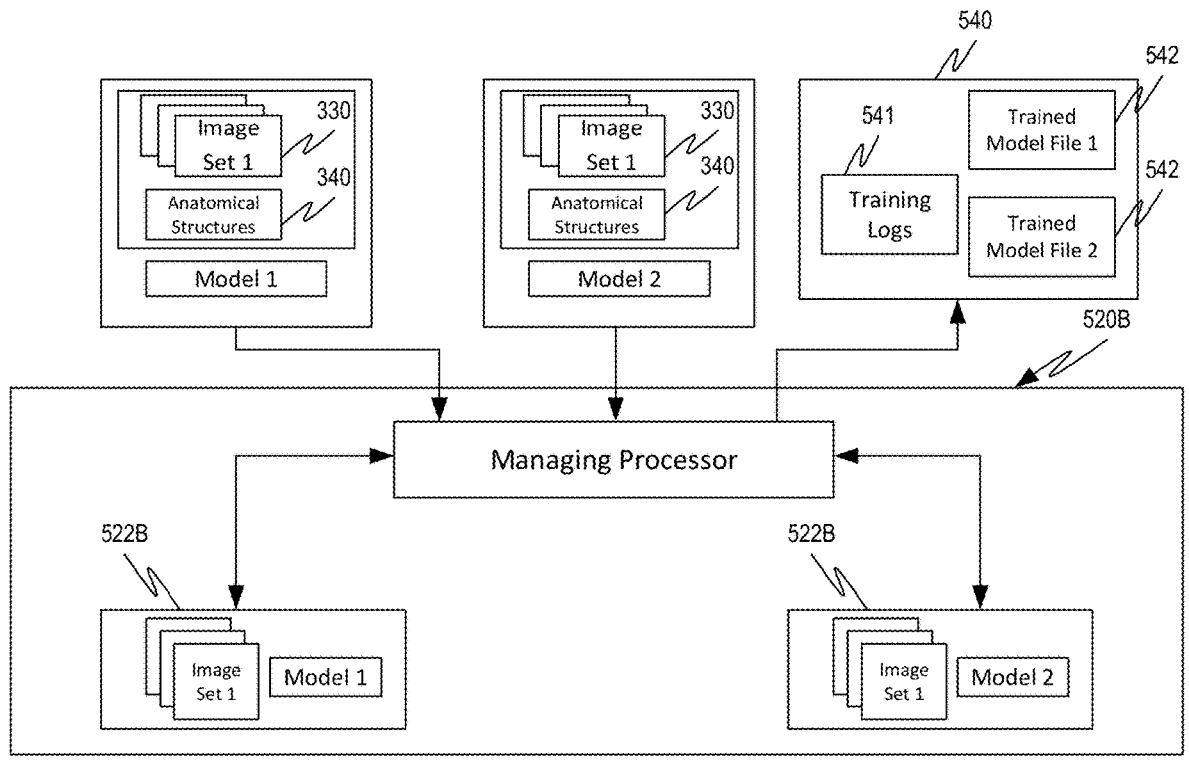

In another embodiment where an image data set 330 is used to train a first and a second segmentation DNN model (Model 1, Model 2), as shown in FIG. 12E, the image data set 330 can be replicated across a first virtual machine 522B and a second virtual machine 522B, and the first virtual machine 522B can hold the first model (Model 1) and the second virtual machine 522B can hold the second model (Model 2). Each of the virtual machines performs forward and backward passes without passing information between the virtual machines. When a virtual machine 522B finishes the process, the value obtained is used to calculate the updated weights of their respective image data sets 330, 350. The results 540, which can include training logs 541 and respective trained model files 542 (i.e., Model File 1, Model File 2), can be made accessible to the user of the client computing device 100 via the computing system/network 400.

Figure 12F:
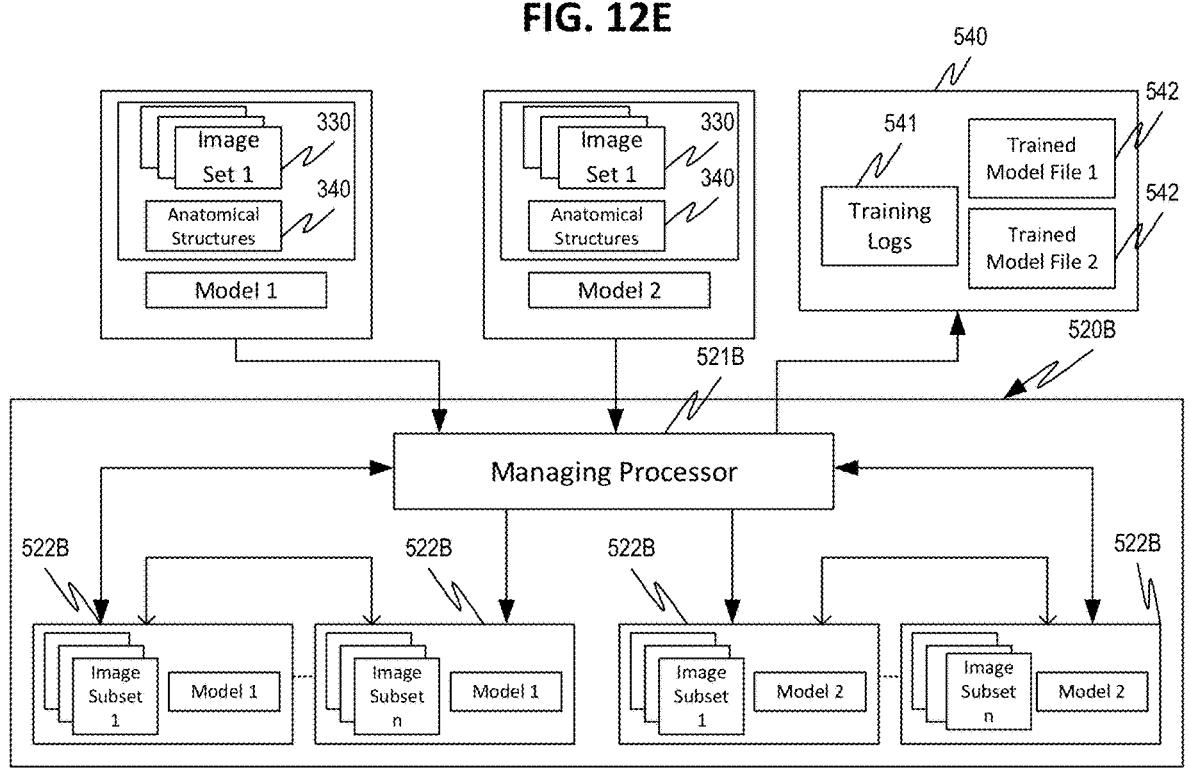

In an alternative configuration, as shown in FIG. 12F, the image data set 330 can be divided into n image subsets (Image Subset 1-Image Subset n) across n virtual machines 522B, and the first and second models (Model 1, Model 2) are replicated across respective sets of n virtual machines 522B. In operation, the first set of virtual machines 522B performs forward and backward passes for each image subset 523. When a virtual machine 522B finishes the process, it shares the updates with the other virtual machines 522B, and the obtained values are used to calculate the updated weights of the entire image data set 330, and the weights are synchronized across the replicated models 120/411/412. The results 540 which can include a training log 541 and a trained model file 542 can be made accessible to the user of the client computing device 100 via the computing system/network 400. The number n of the virtual machines to be used can be determined based on the size of the image data set 330, and/or other applicable considerations. The number of virtual machines 522B to be used can also be determined based on data size of one or more segmentation requests, and/or size of the segmentation model to be trained, and/or the number of segmentation requests.

In the application deployment configurations of FIGS. 12A-12F, the updates at the different virtual machines 522B can be made in a synchronous or asynchronous fashion.

Although specific deployment configurations have been illustrated in FIGS. 12A-12F, it is to be understood that any other combination of data-parallel and/or model-parallel deployment configurations across n virtual machines are possible, and that any and all the possible configurations are encompassed herein. Additionally, it is to be understood that the scaling of the computing resources, such as the virtual machines in the cloud resources 500, up and down, can be made according to the need, which includes data size of one or more segmentation requests, and/or size of the segmentation model to be trained, and/or the number of segmentation requests.

It is also to be understood that the computing system/network 400 can be the managing processor 521B, and that the managing processor 521B and/or the computing system/network 400 is configured to manage the clusters of virtual machines 522B, gather the results 540, scale the resources, manage the monitoring of the training process, and handle any failures in the segmentation training process.

In one or more embodiments, the computing system/network 400 is further configured to enable a user of the client computing device 100 to securely access the training logs 541 so that the user is able to monitor the progress of the segmentation model training process. The training logs 541 can be directly accessed through the web interface 200 or can be downloaded or streamed through the computing system/network 400.

In one or more embodiments, the computing system/network 400 is further configured to allow a user of the client computing device 100 to stop the training of the segmentation DNN model through the web-interface 200.

Figure 13A:
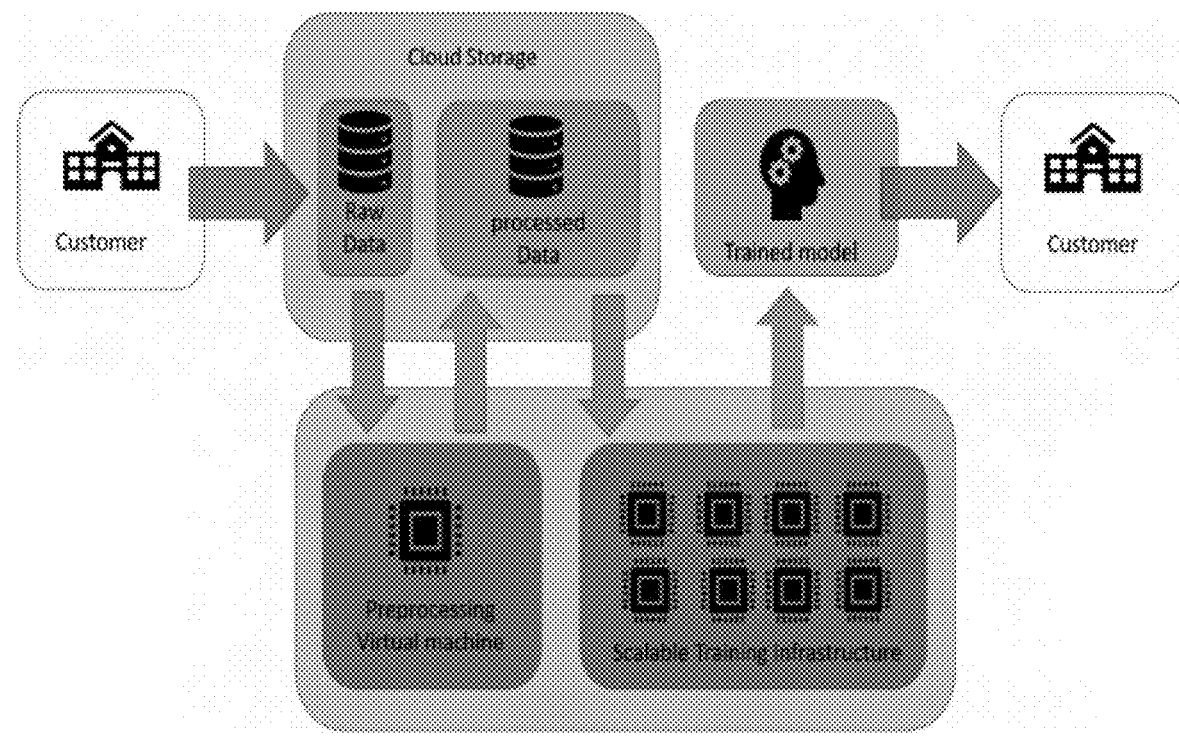
FIGS. 13A-13C are process flow diagrams for cloud-based scalable segmentation DNN model training solutions, according to various embodiments of the disclosed subject matter.
Figure 13B:
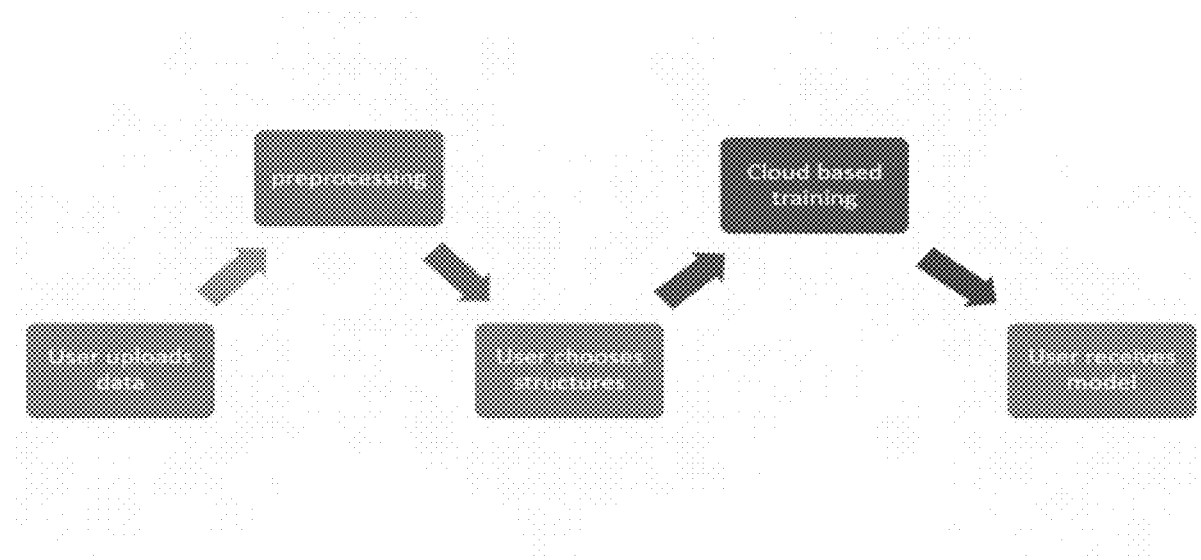
Figure 13C:
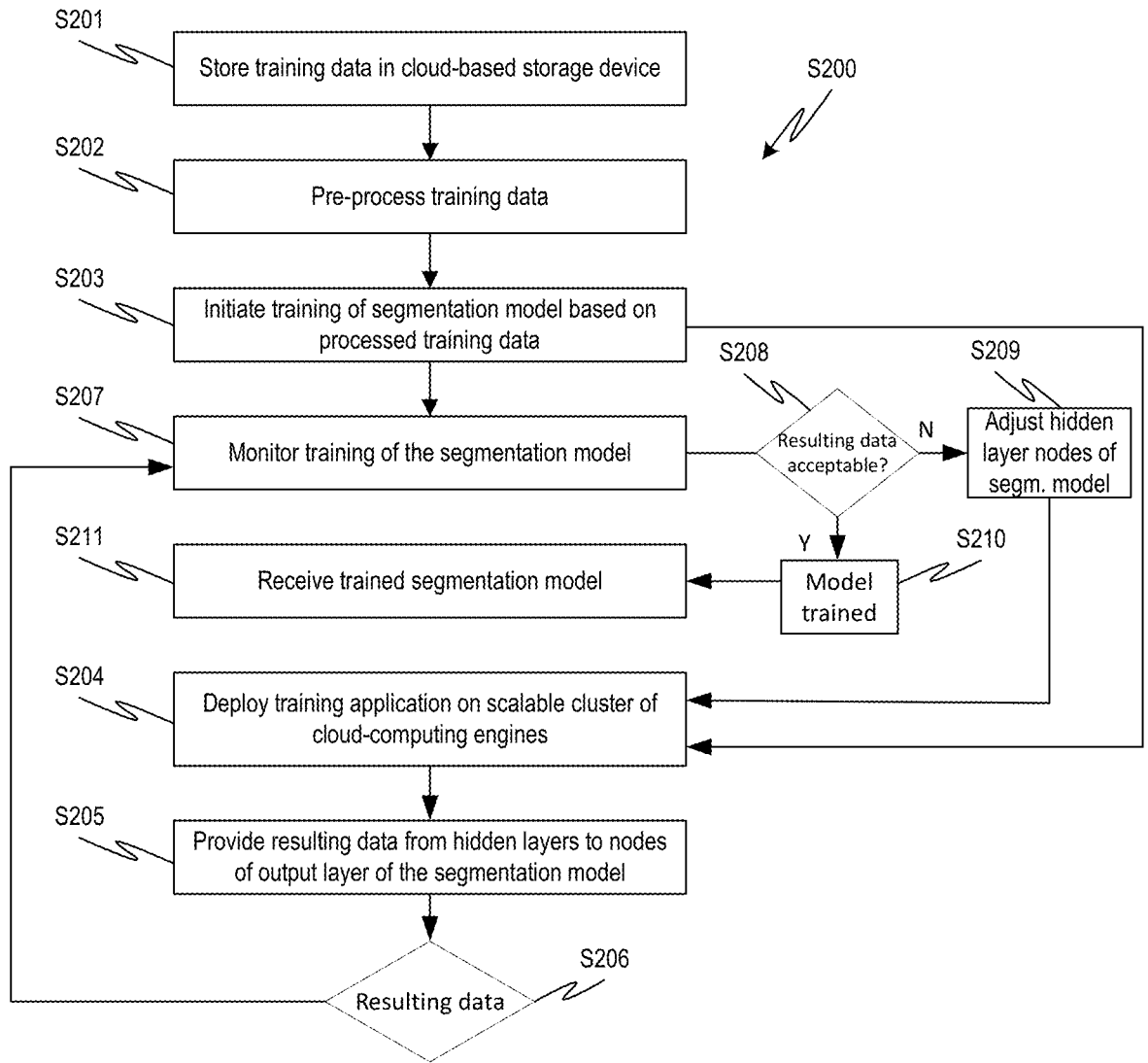

Referring to FIGS. 13A-13C, exemplary operations of a segmentation model training will be described. FIGS. 13A and 13C are generalized schematic illustrations of a cloud-based segmentation model training operation. In a first step, a customer can securely upload raw data, such as, but not limited to, training data desired to be used for training the segmentation model, to a secure cloud storage place. The uploaded raw data can next be pre-processed using cloud-based computing resources, such as, but not limited to, virtual machines. The processed data can be securely stored back into the cloud-based storage. The customer can next choose the target anatomical structures and provides access to the processed trained data. A cloud-based computing network including a scalable training infrastructure can next access the processed trained data so that the segmentation model can be trained using a plurality of computing machines, such as, but not limited to, a cluster of managed virtual machines, to generate a trained segmentation model based on the processed data and the selected anatomical structures. The trained model is then made accessible to the customer for further use.

FIG. 13C is an exemplary process flow S200 diagram for various steps underlying the training of a segmentation DNN model of FIGS. 13A-13B. The process S200 can begin with step S201 where a user is prompted via a web-interface to upload a training dataset to a secure cloud storage device. Alternatively, in the case where the training dataset has been previously uploaded to the cloud storage device, the initial prompting can be bypassed.

The training dataset can include a set of two-dimensional (2-D) or three-dimensional (3-D) medical images or image slices with ground truth contours for the anatomical structures imaged by the different pixels or voxels. The training dataset can have images that have already been segmented (i.e., contoured), where a ground truth label map provides a known anatomical structure label for each pixel of a representative image slice of the training image. In other words, pixels of the ground truth label map can be associated with known anatomical structures.

Together with the set of medical images, a list of anatomical structures is also uploaded to the cloud storage device together with the segmentation model desired to be trained. In embodiments, the training dataset includes the set of medical images and the list of anatomical structures. The training dataset can further include additional ground truth information, such as cut-off plane location and/or user-defined ROIs (e.g., bounding boxes), for example.

In step S202, the pre-processing of the training data can be initiated. The pre-processing can be initiated by the user via the web-interface by selecting a pre-processing option displayed to the user on a display screen of the computing device 100. The pre-processing option may be displayed to the user after the uploading of the training dataset to the cloud storage device is terminated, or as a first step of the training process initiation of S203. The user may be given the option to select one or more of the available pre-processing operations. Alternatively, the pre-processing operation includes a previously determined set of pre-processing operations.

The user is then given the option, via the web-interface for example, to initiate a segmentation DNN model training process in S203. Upon selecting the training option, the user may be prompted to select the target anatomical structures from the stored list of anatomical structures. Upon selection of the target anatomical structures, a training application is initiated in S204 by which the framework supporting communication and flow of data between the different devices, platforms and networks, as well as the operations and tasks necessary for the training process is deployed on a scalable cluster of cloud-computing devices. By deploying the training application, the processed training data associated with the target anatomical structures and the segmentation model from the cloud storage device are used as input data across a plurality of cloud computing devices. The deploying can be done across as few or as many cloud computing devices as necessary. The scaling up or down of the computing devices can be done based on the number of training requests received and/or based on the number of tasks each computing device would need to perform and/or based on the complexity of each request and/or task, for example. The computing system/network 400 is configured to determine the computing resources 520 needed for each request and appropriately scale the computing resources 520.

The training process includes determining one or more parameters of nodes in hidden layers of the segmentation DNN model, for example, by an iterative process that varies parameters such that the segmentation DNN model output more closely matches corresponding ground truth. For example, nodes in the hidden layer can include a filter or kernel, parameters of which (e.g., kernel weight, size, shape, or structure) can be adjusted during the training process.

In an exemplary embodiment, each hidden layer of the segmentation DNN model may be represented by a virtual machine of a cloud computing cluster that mimics a neural DNN engine. During the iterative model training process, the training data is propagated through the nodes of hidden layers of the input DNN model (i.e., through the virtual machines), and the resulting data from the hidden layer are provided to nodes of the output layer of the DNN model in S205 (i.e., the results from each virtual machine). The resulting data from the output layer S206 (i.e., the resulting contours) can be monitored in S207 by the user via the training logs (541), for example, in order to determine in S208 whether the resulting data is acceptable. The aim of training S204 is to train the segmentation DNN model to perform automatic segmentation of anatomical structures in the image(s) by mapping the input data (i.e., medical images) to example output data (i.e., ground truth contours). In some embodiments, the training S204 can involve finding weights that minimize the training error (e.g., as determined by loss function for example) between ground truth contours and estimated contours generated by the deep learning engines.

In one or more embodiments, the user may determine that the resulting data S206 is acceptable by comparing the resulting data with the ground truth via a loss function.

Alternatively, the user may determine in S208 that the resulting data S206 is acceptable by comparing the resulting data S206 with a resulting data obtained by applying an existing model (previously determined model stored in a database, for example) on the processed training data, or by applying an existing model on an existing training dataset, for example.

Alternatively, the user may determine whether the resulting data S206 is acceptable by comparing it with a predetermined threshold, for example.

Alternatively, the user may also set a predetermined number of iterations to obtain the resulting data in S206 and when the iteration number has been reached, the resulting data is accepted.

Alternatively, the user may determine whether the resulting data S206 is acceptable by verifying during the training feedback received via the training logs 541 how well the output matches a correct/desired/wanted/threshold output.

Once the user accepts in S208 the resulting data, whether by determining that the loss function meets a predetermined threshold, a threshold number of iterations has been reached, no further improvement is seen between iterations, or no further improvement is seen between it and the compared results, the segmentation DNN model can be fixed at S210. The trained segmentation DNN model can be provided to the user in S211 for downloading or streaming, or to have access to it via an additional service in S211. Otherwise, the training S200 proceeds to S209, where the segmentation DNN model is modified, e.g., by adjusting parameters of the hidden layer nodes, in order to improve the match between output and the desired output. The training process S204 can iterate repeatedly until the desired iteration criteria is met at S208. The segmentation DNN model is then considered trained.

The trained segmentation DNN model of S210 can also be stored in an image segmentation model database of the computing system/network 400, or that of the client computing device 100, or that of a secure cloud storage 300.

Once execution of the model training is finished and/or terminated by the user, the trained segmentation DNN model S210 can be provided to the client computing device 100 to be further used for inference to predict contours of anatomical structures for a patient.

Figure 14:
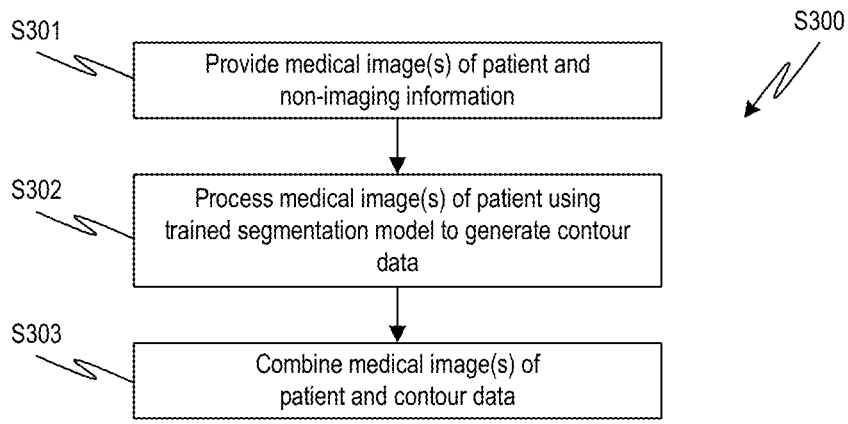
FIG. 14 is a process flow diagram for an inference phase using a trained segmentation DNN model, according to various embodiments of the disclosed subject matter.

An exemplary inference process S300 is shown in FIG. 14. The process S300 uses the trained segmentation DNN models of S210, for example, to process medical image(s) of a patient to automatically segment (i.e., contour) unknown anatomical structures shown therein. In inference phase, the process S300 can begin at S301, where a patient data set including one or more medical image(s) are provided to the trained segmentation DNN model S210. The image(s) of the patient can be obtained using any medical imaging modality and do not necessarily need to be of the same modality as images used to train the segmentation DNN model.

Process S300 can then proceed to S302, where the medical image(s) are processed by the trained segmentation DNN model S210 and outputs contour data based on its training. In some embodiments, the contour data may be combined with the original medical image(s) at S303, such that the contours are overlaid on the corresponding anatomical structures in the image, for example, for visualization by a user or for use in radiation treatment planning. Alternatively, the segmentation DNN model S210 may directly produce the contours on the medical images as an output without separate combination step S303.

In embodiments, the inference process is deployed by the system/network 400, via the inference engine 409, on one or more computing resources 520.

Alternatively, or additionally, the inference process is deployed by the client computing device 200 using the inference engine 112.

Alternatively, or additionally, in some embodiments, non-imaging information can be used along with the medical image(s) of the patient in the inference phase. For example, non-imaging information, such as field parameters for a planned radiotherapy, can be used to define appropriate cutting planes. In radiotherapy planning, the out of field part of anatomical structures might not be of interest, depending on if the organ is serial or parallel. The out of field cut-off plane can be detected if the field geometry is known. In particular, at S301, the one or more medical image(s) can be provided along with the non-imaging information. The non-imaging information can be provided to the trained segmentation DNN model S210, for example, for use in generating contour data in S302.

It will be appreciated that a cloud-based system and method is provided for training a segmentation model, comprising: an interface configured to allow a user to upload and store training data in a storage device of a cloud-based network; provide access to the training data stored in the storage device; initiate a request for training a segmentation model; monitor the training of the segmentation model; and download the trained segmentation model; and a computing infrastructure configured to: pre-process the training data using a first set of computing resources of the cloud-based network to obtain processed training data, and store the processed training data in the storage device; deploy a training application on a second set of computing resources of the cloud-based network to train the segmentation model based on the processed training data;

provide access to monitor the training; and provide access to the trained segmentation model.

It will also be appreciated that a cloud-based scalable system and method is provided for training a segmentation model, the system configured to: access training data stored in a storage device of a cloud-based network; pre-process the training data using a first set of computing resources of the cloud-based network, and store the pre-processed training data in the storage device; deploy a training application on a second set of computing resources of the cloud-based network to train the segmentation model based on the pre-processed training data; provide access to monitor the training of the segmentation model; and provide access to the trained segmentation model.

It will also be appreciated that a system for training a segmentation model is provided, the system comprising: an interface configured to allow a user to select training data from a database, and initiate a request to train a segmentation model using the selected training data; and a computing infrastructure configured to pre-process the selected training data, deploy a training application to train the segmentation model based on the pre-processed training data, and provide access to the trained segmentation model.

The training application may include one or more machine learning frameworks configured to support deployment of data and computations across different platforms and different tasks.

The segmentation model to be trained may be provided by the user through the interface.

The selected training data can include a plurality of medical images and a plurality of anatomical structures.

The automatic segmentation model can be a segmentation neural network model.

The training can include training the segmentation neural network model to approximate contours of selected anatomical structures in the medical images.

It will also be appreciated that a system for training a segmentation model is provided, the system being configured to: access training data stored in a storage device of a cloud-based network; pre-process the training data using a first set of computing resources of the cloud-based network, and store the pre-processed training data in the storage device; deploy a training application on a second set of computing resources of the cloud-based network to train the segmentation model based on the pre-processed training data; provide access to monitor the training of the segmentation model; and provide access to the trained segmentation model.

The first set of computing resources may include a computing device, a computing server, or a virtual machine.

The second set of computing resources may include one or more virtual machines.

The second set of computing resources may include a scalable cluster of computing engines including a managing computing engine and a plurality of working computing engines.

The cluster may be configured to be scaled based on number of segmentation model training requests.

The training application may include one or more machine learning frameworks configured to support deployment of computations across different platforms and different tasks.

The deploying of the training application may be initiated at a remote device through a web-based training interface.

The training data may be received from the remote device, and access to the training data may be provided by the remote device.

The segmentation model to be trained may be received from the remote device.

The segmentation model to be trained can be provided by the system.

The system may be further configured to provide a plurality of segmentation models and to allow selection by the remote device via web-based training interface of one or more segmentation models from the set for training.

The training data may include a medical image set including a plurality of medical images, and an anatomical structure set including a plurality of anatomical structures.

The segmentation model may be an automatic segmentation model.

The automatic segmentation model may be a segmentation neural network model.

The training may include training the segmentation neural network model to approximate contours of different anatomical structures in the medical images.

The different anatomical structures to be contoured can be selected from the set of anatomical structures stored in the storage device.

The selection can be made at the remote device via a network interface.

The anatomical structures may include one or more of targets, organs, tissues, blood vessels, and bones.

The providing access to monitor the training can include providing output checkpoints at different intervals during training or at a request from the remote device.

The system may be further configured to provide information regarding training progress, training performance, and training completion.

The system may be further configured to apply the trained segmentation model on a dataset and a different segmentation model on the dataset, compare the results, and provide the compared results as the information regarding training performance.

It will also be appreciated that a method for cloud-based training of a segmentation model is provided, comprising: uploading and storing training data in a storage device of a cloud-based network; initiating a request for training a segmentation model; the initiation automatically deploying a training application on computing resources of the cloud-based network by which the segmentation model is trained using the stored training data; monitoring the training; and accessing to the trained segmentation model.

It will also be appreciated that a non-transitory computer-readable storage medium is also disclosed upon which is embodied a sequence of programmed instructions, and a computer processing system that executes the sequence of programmed instructions embodied on the computer-readable storage medium to cause the computer processing system to execute any one or a combination of the herein described method steps, using a system as described herein.

It will be appreciated that the aspects of the disclosed subject matter can be implemented, fully or partially, in hardware, hardware programmed by software, software instruction stored on a computer readable medium (e.g., a non-transitory computer readable medium), or any combination of the above. For example, components of the disclosed subject matter, including components such as a controller, module, model, neural network, or any other feature, can include, but are not limited to, a personal computer or workstation or other such computing system that includes a processor (e.g., graphics processing unit), microprocessor, microcontroller device, or is comprised of control logic including integrated circuits such as, for example, an application specific integrated circuit (ASIC). Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of any process, method, or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of any process, method, or algorithm disclosed herein may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A system for training a segmentation model, comprising:
  an interface configured to allow a user to:
    upload and store training data in a storage device of a cloud-based network;
    provide access to the training data stored in the storage device;
    initiate a request for training a segmentation model;
    monitor the training of the segmentation model; and
    download the trained segmentation model; and
  a computing infrastructure configured to:
    pre-process the training data using a first set of computing resources of the cloud-based network to obtain processed training data, and store the processed training data in the storage device;
    deploy a training application on a second set of computing resources of the cloud-based network to train the segmentation model based on the processed training data;
    provide access to monitor the training; and
    provide access to the trained segmentation model,
  wherein the pre-processing of the training data includes applying one or more operations from a plurality of operations to transform the training data into a representation that is processable by the second set of computing resources, and
  wherein the plurality of operations are configured to be displayed on a display device for selection by the user via the interface,
  the selection being made based on the second set of computing resources.

2. The system of claim 1, wherein the interface is a web-based interface.

3. The system of claim 1, wherein the first set of computing resources includes a computing device, a computing server, or a virtual machine.

4. The system of claim 1, wherein the second set of computing resources includes one or more virtual machines.

5. The system of claim 1, wherein the second set of computing resources includes a scalable cluster of computing engines including a managing computing engine and a plurality of working computing engines, the cluster being configured to be scaled up or down in order to deploy the training application across as many of the working computing engines as the computing infrastructure determines to be necessary, wherein the computing infrastructure determines how many of the working computing engines are necessary based on one or more of number of segmentation model training requests, complexity of each request, and amount of task needed to be performed by each of the plurality of computing engines.

6. The system of claim 1, wherein the training application includes one or more machine learning frameworks configured to support deployment of data and computations across different platforms and different tasks.

7. The system of claim 1, wherein the segmentation model to be trained is provided by the user through the interface.

8. The system of claim 7, wherein the segmentation model to be trained is selected via the interface from a plurality of segmentation models provided to the user by the computing infrastructure.

9. The system of claim 1, wherein the training data includes a medical image set including a plurality of medical images, and an anatomical structure set including a plurality of anatomical structures.

10. The system of claim 9, wherein the segmentation model is an automatic segmentation model.

11. The system of claim 10, wherein the automatic segmentation model is a segmentation neural network model.

12. The system of claim 11, wherein the training includes training the segmentation neural network model to approximate contours of the plurality of anatomical structures in the plurality of medical images.

13. The system of claim 12, wherein the anatomical structures include one or more of organs, tissues, blood vessels, and bones.

14. The system of claim 1, wherein the providing access to monitor the training includes providing output checkpoints at different intervals during training or at the request of the user.

15. The system of claim 14, wherein the computing infrastructure is further configured to provide access to information regarding training progress, training performance, and training completion.

16. The system of claim 15, further configured to:
apply the trained segmentation model on a dataset obtained from the user;
apply another segmentation model on the dataset obtained from the user;
compare results from the trained segmentation model and the another segmentation model applied on the dataset obtained from the user to obtain a comparison result; and
evaluate the comparison result against a predetermined threshold value.

17. The system of claim 15, further configured to:
apply the trained segmentation model on a dataset obtained from the user; and
evaluate a segmentation result obtained from applying the trained segmentation model on the dataset obtained from the user against a predetermined threshold value.

18. The system of claim 1, wherein the providing access to the trained segmentation model includes providing a training log and a model file to the user for downloading the trained segmentation model.

19. A method for cloud-based training of a segmentation model, comprising:
uploading and storing training data in a storage device of a cloud-based network;
initiating at least one request for training a segmentation model;
determining how many computing resources of the cloud-based network are needed to train the segmentation model, the determining being made based on one or more of data size of the request, size of the segmentation model to be trained, number of segmentation requests, and complexity of each request;
automatically deploying a training application on as many computing resources of the cloud-based network as determined to be needed, to train the segmentation model using the stored training data;
monitoring the training; and
accessing the trained segmentation model.

20. A non-transitory computer-readable storage medium upon which is embodied a sequence of programmed instructions, and a computer processing system that executes the sequence of programmed instructions embodied on the computer-readable storage medium to cause the computer processing system to:
access training data uploaded by a client to a cloud storage device;
determine how many cloud-based computing resources are needed to train a segmentation deep neural network (DNN) model, the determining being made based on one or more of data size of a request to train the segmentation (DNN) model, size of the segmentation (DNN) model, and complexity of the request;
deploy a training application on as many cloud-based computing resources as determined to be needed to train the segmentation deep neural network (DNN) model based on the training data;
allow monitoring of the training data by the client;
allow the client to determine whether the segmentation (DNN), model is trained; and
provide the trained segmentation (DNN), model to the client.

* * * * *